(12) United States Patent
Poponin

(10) Patent No.: US 8,383,416 B2
(45) Date of Patent: Feb. 26, 2013

(54) MICROBEAD OPTICAL SENSOR WITH LAYERED PLASMON STRUCTURE FOR ENHANCED DETECTION OF CHEMICAL GROUPS BY SERS

(75) Inventor: Vladimir Poponin, Costa Mesa, CA (US)

(73) Assignee: Vladimir Poponin, Costa Mesa, CA (US)

( * ) Notice: Subject to any disclaimer, the term of this patent is extended or adjusted under 35 U.S.C. 154(b) by 15 days.

(21) Appl. No.: 13/347,566

(22) Filed: Jan. 10, 2012

(65) Prior Publication Data

US 2012/0107958 A1     May 3, 2012

Related U.S. Application Data

(63) Continuation of application No. 12/794,622, filed on Jun. 4, 2010, now Pat. No. 8,093,065, which is a continuation of application No. 12/059,736, filed on Mar. 31, 2008, now abandoned, which is a continuation of application No. 11/133,632, filed on May 19, 2005, now Pat. No. 7,351,588.

(60) Provisional application No. 60/572,959, filed on May 19, 2004.

(51) Int. Cl.
*G01N 21/76* (2006.01)

(52) U.S. Cl. ........ 436/172; 436/164; 436/171; 436/524; 436/525; 422/68.1; 422/82.05; 422/82.11

(58) Field of Classification Search .................. None
See application file for complete search history.

(56) References Cited

U.S. PATENT DOCUMENTS

| 5,023,139 A | 6/1991 | Birnboim et al. |
| 5,478,755 A | 12/1995 | Altridge et al. |

(Continued)

FOREIGN PATENT DOCUMENTS

| EP | 0 327 843 B1 | 8/1989 |
| JP | 11-237391 | 8/1999 |

(Continued)

OTHER PUBLICATIONS

The International Search Report from PCT/US2004/010544 mailed Jan. 7, 2005.

(Continued)

*Primary Examiner* — Robert Xu
(74) *Attorney, Agent, or Firm* — King & Spalding LLP; Peter Dehlinger

(57) ABSTRACT

An optical sensor and method for use with a visible-light laser excitation beam and a Raman spectroscopy detector, for detecting the presence chemical groups in an analyte applied to the sensor are disclosed. The sensor includes a substrate, a plasmon resonance mirror formed on a sensor surface of the substrate, a plasmon resonance particle layer disposed over the mirror, and an optically transparent dielectric layer about 2-40 nm thick separating the mirror and particle layer. The particle layer is composed of a periodic array of plasmon resonance particles having (i) a coating effective to binding analyte molecules, (ii) substantially uniform particle sizes and shapes in a selected size range between 50-200 nm (ii) a regular periodic particle-to-particle spacing less than the wavelength of the laser excitation beam. The device is capable of detecting analyte with an amplification factor of up to $10^{12}$-$10^{14}$, allowing detection of single analyte molecules.

7 Claims, 20 Drawing Sheets

U.S. PATENT DOCUMENTS

| | | | |
|---|---|---|---|
| 5,479,024 | A | 12/1995 | Hillner et al. |
| 5,552,086 | A | 9/1996 | Siiman et al. |
| 5,611,998 | A | 3/1997 | Aussenegg et al. |
| 6,002,471 | A | 12/1999 | Quake et al. |
| 6,149,868 | A | 11/2000 | Natan et al. |
| 6,180,415 | B1 | 1/2001 | Schultz et al. |
| 6,242,264 | B1 | 6/2001 | Natan et al. |
| 6,344,272 | B1 | 2/2002 | Oldenburg et al. |
| 6,441,359 | B1 | 8/2002 | Cozier et al. |
| 6,514,767 | B1 | 2/2003 | Natan |
| 6,850,323 | B2 | 2/2005 | Anderson |
| 7,151,598 | B2 | 12/2006 | Poponin |
| 7,351,588 | B2 | 4/2008 | Poponin |
| 2002/0142480 | A1* | 10/2002 | Natan ............ 436/171 |
| 2003/0174384 | A1 | 9/2003 | Halas et al. |
| 2003/0228682 | A1 | 12/2003 | Lakowicz et al. |
| 2003/0232388 | A1 | 12/2003 | Kreimer et al. |
| 2004/0174521 | A1 | 9/2004 | Drachev et al. |

FOREIGN PATENT DOCUMENTS

| | | |
|---|---|---|
| JP | 2001-165852 | 6/2001 |
| JP | 2002-055041 | 2/2002 |
| JP | 2002-207000 | 7/2002 |
| WO | WO 99/20789 A1 | 4/1999 |
| WO | WO 99/51960 A2 | 10/1999 |
| WO | WO 2004/090505 A2 | 10/2004 |
| WO | WO 2005/033335 A2 | 4/2005 |
| WO | WO 2007/011389 A2 | 1/2007 |

OTHER PUBLICATIONS

The International Search Report from PCT/US2005/0017981 mailed Aug. 21, 2006.
The International Search Report from PCT/US2005/035980 mailed Feb. 9, 2007.
The Notice to Grant for Russian application RI 2006144957, 13 pages dated Feb. 16, 2009.
Supplementary European Search Report for Application No. EP 05 75 3332, search completed Mar. 19, 2010.
Aravind et al., "Use of a perfectly conducting sphere to excite the plasmon of a flat surface. 1. Calculation of the local field with applications to surface-enhanced spectroscopy", Journal of Physical Chemistry, vol. 86, pp. 5076-5084 (1982).
Aravind et al., "The effects of the interaction between resonances in the electromagnetic response of a sphere-plane structure—applications to surface enhanced spectroscopy", Surface Science, vol. 124, pp. 506-528 (1983).
Bingler et al., "Interference enhanced surface Raman scattering of adsorbates on a silver-spacer-islands multilayer system", Molecular Physics, vol. 85, No. 3, pp. 587-606 (1995).
Coyle et al., "Localised Plasmons in Gold Photonic Nanocavities", Quantum Electronics and Laser Science, XP010613027, ISBN: 978-1-55752-708-0, p. 257 (2002).
Doering et al., "Single-Molecule and Single-Nanoparticle SERS: Examining the Roles of Surface Active Sites and Chemical Enhancement", Journal of Physical Chemistry, vol. 106, pp. 311-317 (2002).
Félidj et al., "Enhanced substrate-induced coupling in two-dimensional gold nanoparticle arrays", American Physical Soc., Physical Review, vol. 66, No. 24, pp. 245407-1 through 245407-7 (2002).
Futamata et al., "Microscopic morphology and SERS activity of Ag colloidal particles", Vibrational Spectroscopy vol. 30, pp. 17-23 (2002).
Genov et al., "Resonant Field Enhancements from Metal Nanoparticle Arrays", Nano Letters, vol. 4, No. 1, pp. 153-158 (2004).
Gupta et al., "High enhancement factor gold films for surface enhanced Raman spectroscopy", Chemical Physics Letters, vol. 374, pp. 302-306 (2003).
Hardikar et al., "Coating of Nanosize Silver Particles with Silica", J. Colloid Inter. Sci., vol. 221, pp. 133-136 (2000).
Kneipp et al., "Extremely Large Enhancement Factors in Surface-Enhanced Raman Scattering for Molecules on Colloidal Gold Clusters", Applied Spectroscopy vol. 52, pp. 1493-1497 (1998).
Kneipp, et al., "Ultrasensitive chemical analysis by raman spectroscopy", Chem. Rev., vol. 99, pp. 2957-2976 (1999).
Leitner et al., "Optical properties of a metal island film close to a smooth smooth metal surface", Applied Optics, vol. 32, No. 1, pp. 102-110 (1993).
Liz-Marzan et al., "Synthesis of nanosized gold-silica core-shell particles", Langmuir, vol. 12, pp. 4329-4335 (1996).
Markel et al., "Near-field optical spectroscopy of individual surface-plasmon modes in colloid clusters", Physical Review B, vol. 59, pp. 10903-10909 (1999).
Moskovits et al., "SERS and the single molecule", Topics in Applied Physics, vol. 82, pp. 215-226 (2002).
Saito et al., "Simple chemical method for forming silver surfaces with controlled grain sizes for surface plasmon experiments", Langmuir, vol. 19, pp. 6857-6861 (2003).
Steinmuller-Nethl et al., "Enhancement of second harmonic generation in metal islands close to a conducting surface", Applied Physics, vol. 57, pp. 261-265 (1993).
Takemori et al., "Optical response of a sphere coupled to a metal substrate", Journal of the Physical Society of Japan, vol. 56, pp. 1587-1602 (1987).
Wang et al., "The structural basis for giant enhancement enabling single-molecule Raman scattering", PNAS USA, vol. 100, pp. 8638-8643 (2003).
Wasileski et al., "Surface-Enhanced Raman Scattering from Substrates with Conducting or Insulator Overlayers; Electromagnetic Model Predictions and Comparisons with Experiment", Applied Spectroscopy, vol. 54, pp. 761-772 (2000).
Wei et al., "Engineering hotspots for surface enhanced Raman scattering", SPIE, vol. 5221, pp. 92-99 (2003).
Yih et al., "A compact surface plasmon resonance and surface-enhanced Raman scattering sensing device", SPIE, vol. 5327, pp. 5-9 (2004).
Zhang et al., "Orientation Study of Atactic Poly(methyl methacrylate) Thin Film by SERS and RAIR Spectra", Macromolecules, vol. 35, pp. 5140-5144 (2002).
Zheng et al., "Surface-enhanced Raman scattering of 4-aminothiophenol in assemblies of nanosized particles and the macroscopic surface of silver", Langmuir, vol. 19, pp. 632-636 (2003).

* cited by examiner

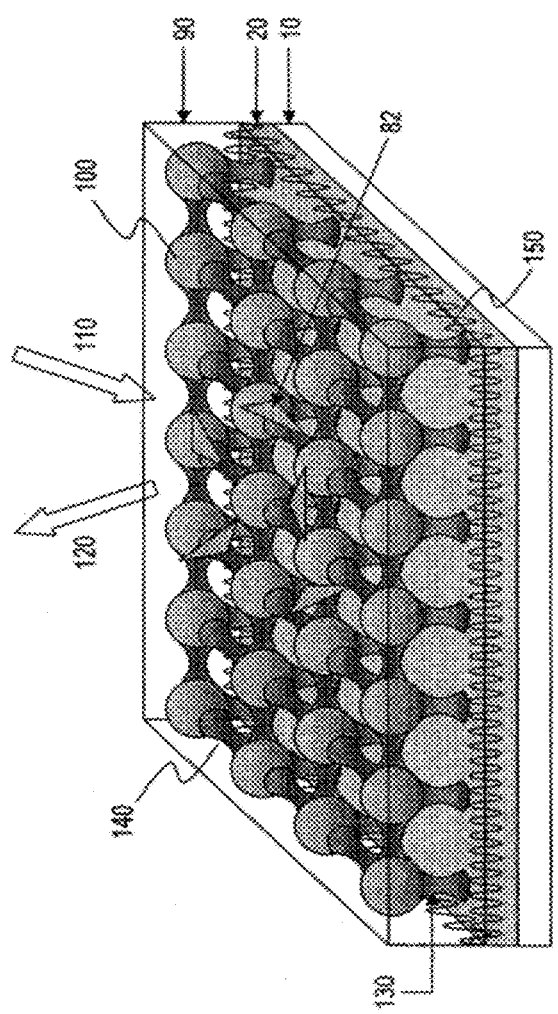
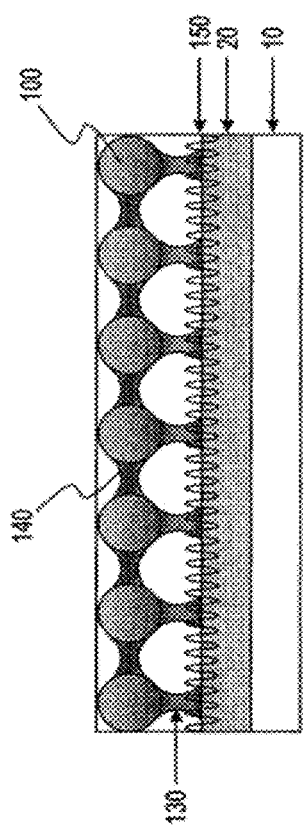
Fig. 2A
Fig. 2B

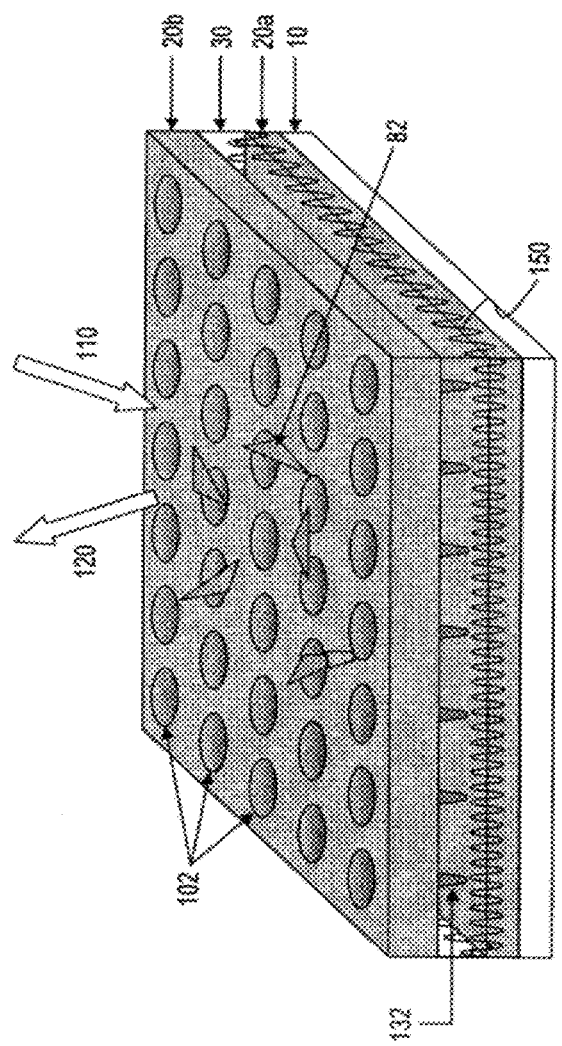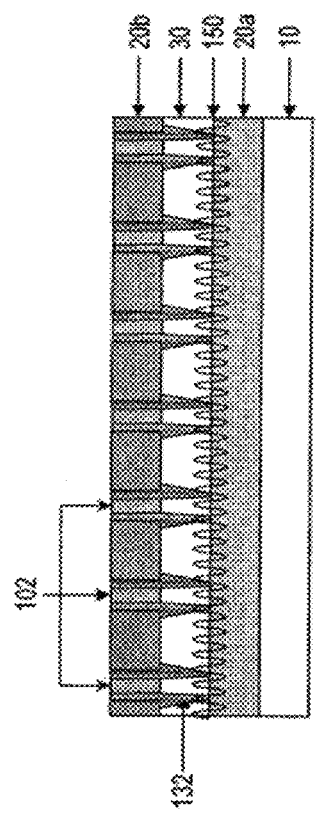
Fig. 3A
Fig. 3B

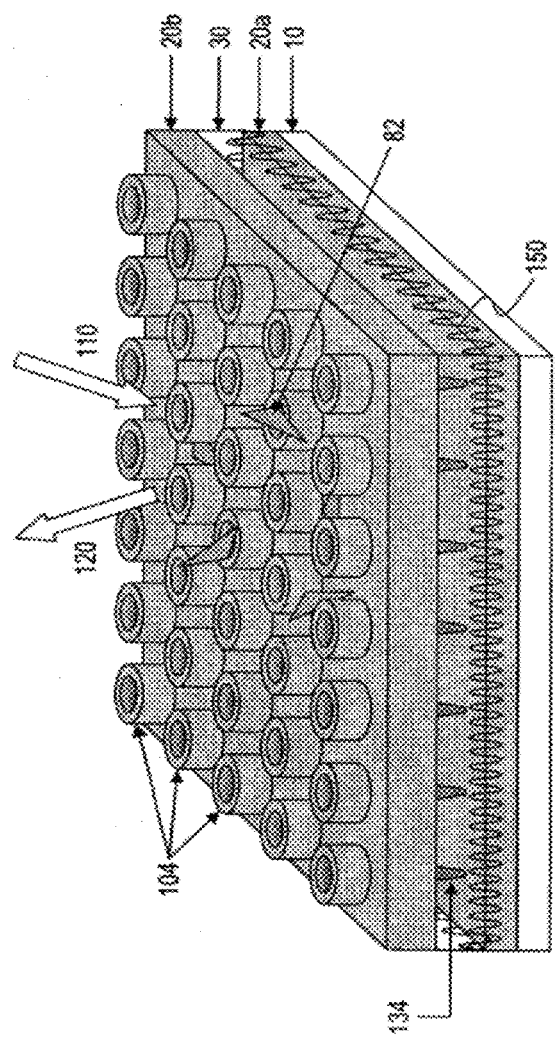
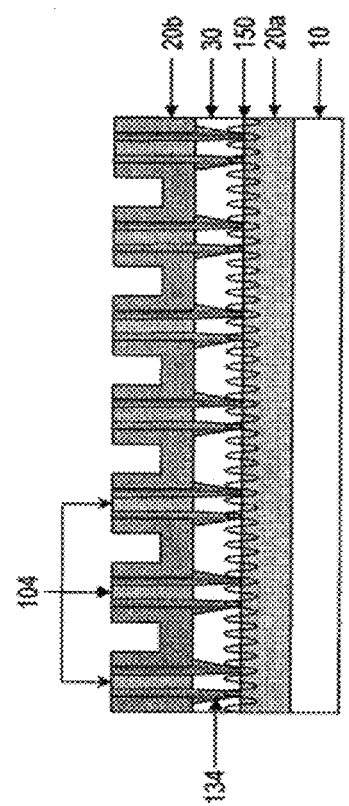
Fig. 4A
Fig. 4B

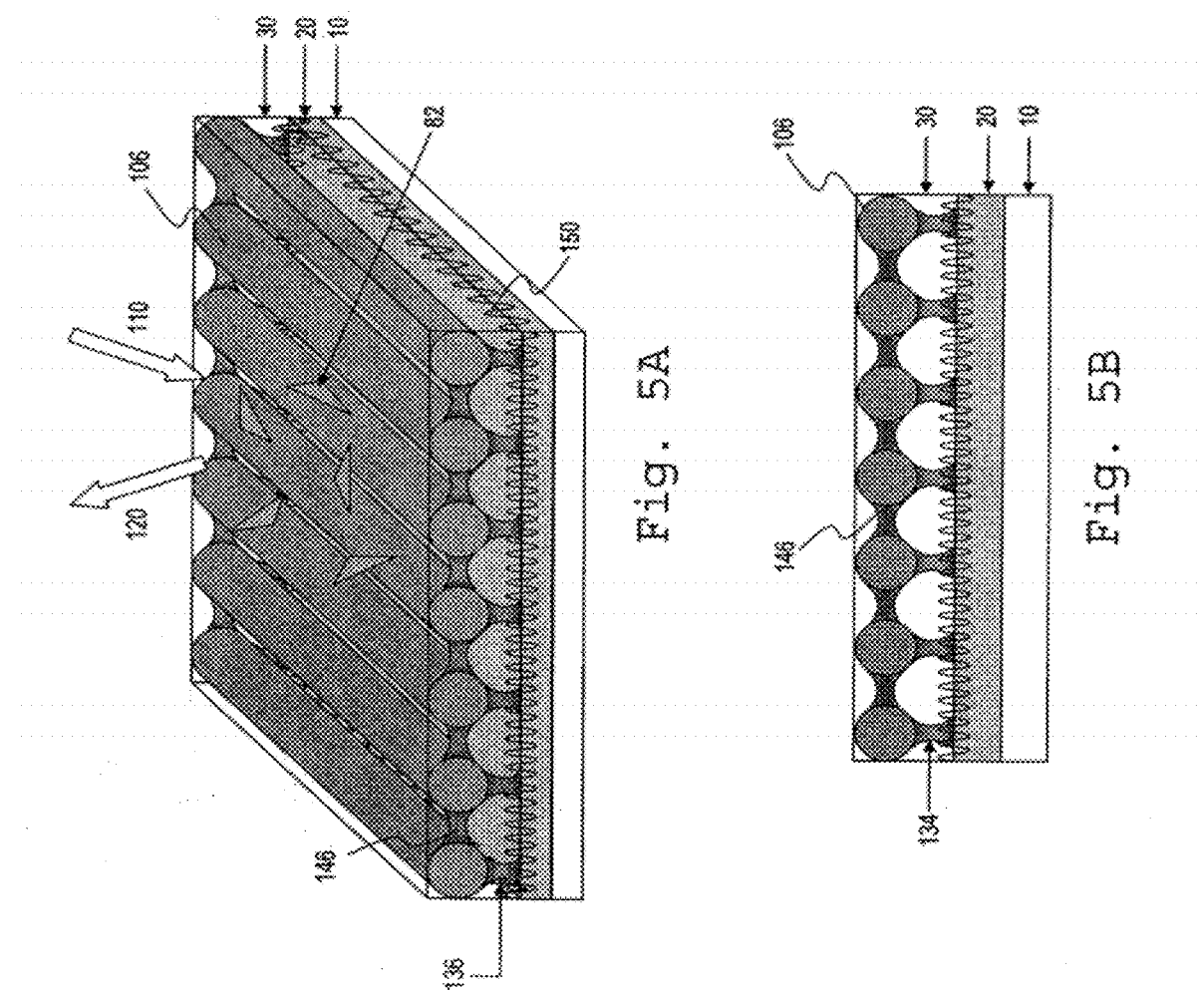

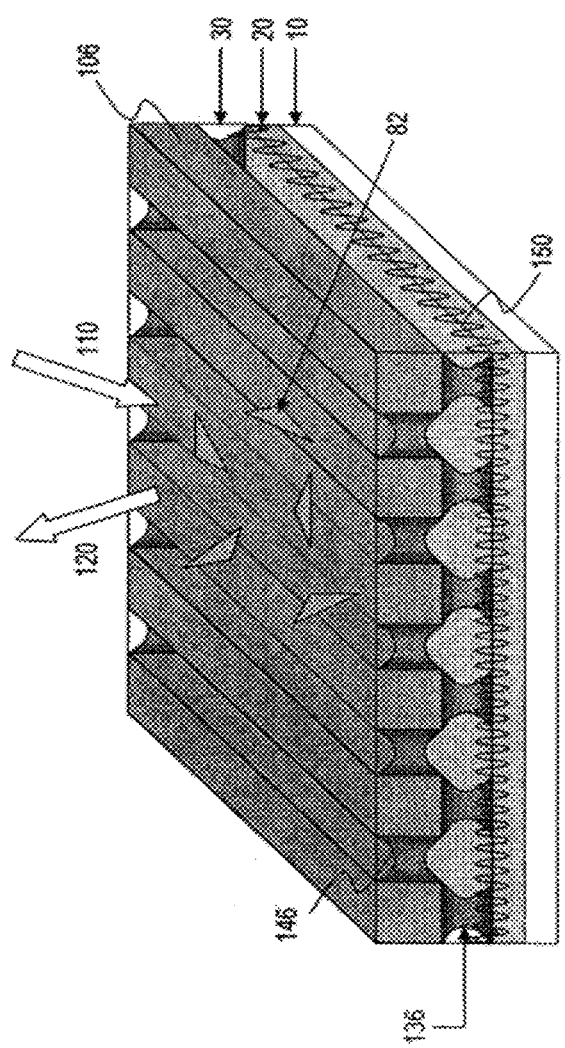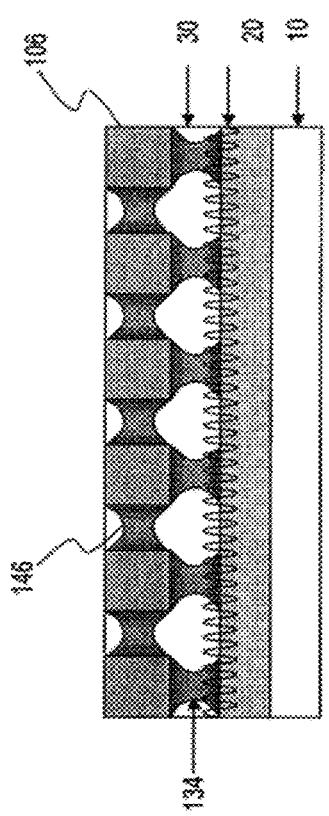
Fig. 5C
Fig. 5D

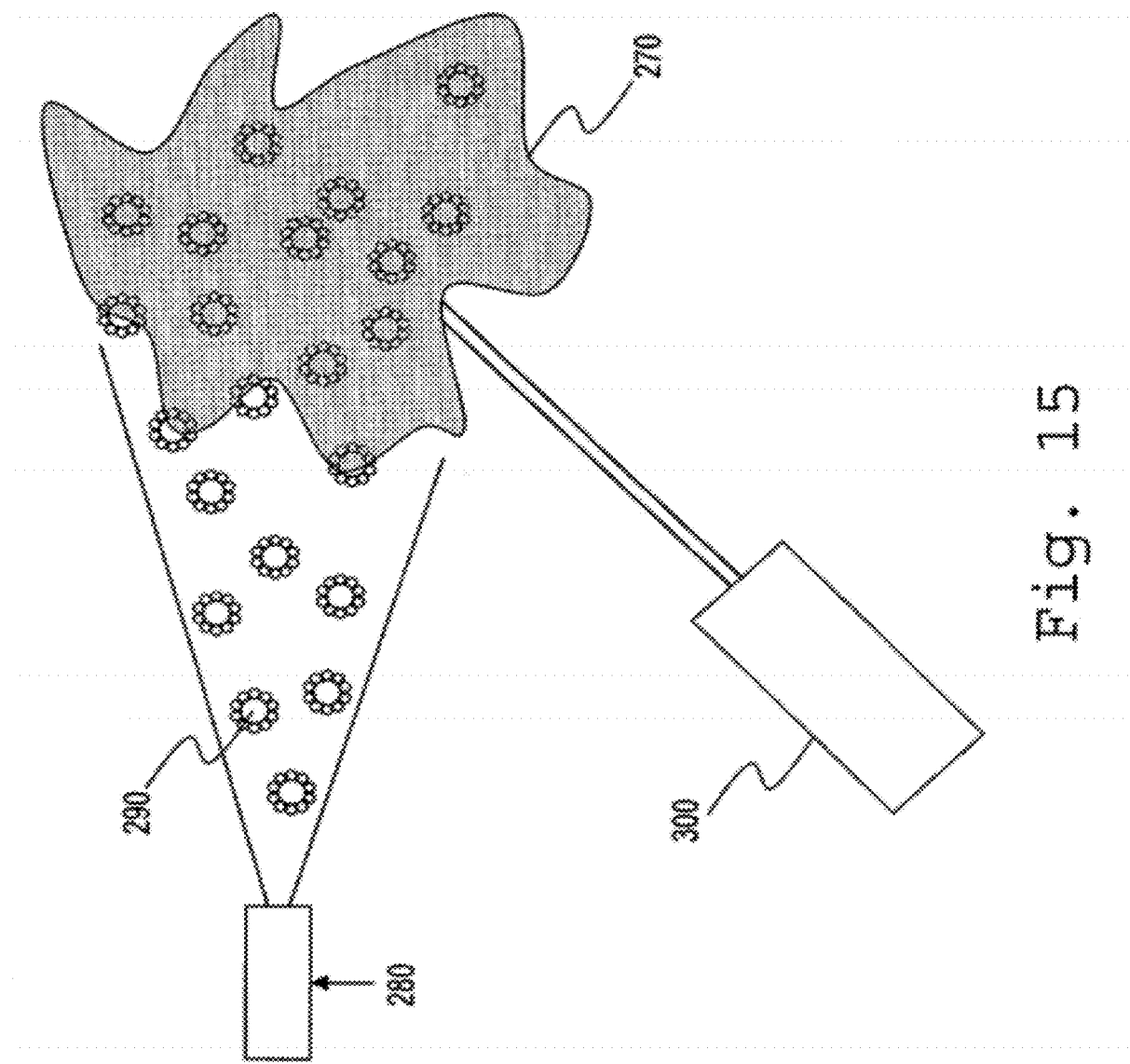

US 8,383,416 B2

MICROBEAD OPTICAL SENSOR WITH LAYERED PLASMON STRUCTURE FOR ENHANCED DETECTION OF CHEMICAL GROUPS BY SERS

This patent application is a continuation of U.S. patent application Ser. No. 12/794,622, filed Jun. 4, 2010, now U.S. Pat. No. 8,093,065, which is a continuation of U.S. patent application Ser. No. 12/059,736, filed Mar. 31, 2008, now abandoned, which is a continuation of U.S. patent application Ser. No. 11/133,632 filed May 19, 2005, now U.S. Pat. No. 7,351,588, which claims priority to U.S. Provisional Patent Application No. 60/572,959 filed May 19, 2004, now abandoned, all of which are incorporated herein in their entirety by reference.

This work was supported in part by U.S. Government Agency and U.S. Department of Defense Air Force Contract No. AFOSR F49620-03-C-0058. The United States Government may have certain rights in this invention.

FIELD OF THE INVENTION

The present invention in general relates to a novel optical sensor composed of SERS-active plasmon particles over a plasmon mirror for enhanced localized optical phenomena, and the use of this effect for ultrasensitive chemical and biological sensing with high structural specificity and with high detection sensitivity.

References

The references below are cited as part of the background of the invention and/or as providing methodologies that may be applied to certain aspects of the present invention. These references are incorporated herein by reference.

G. Bauer et al., "Resonant nanocluster technology-from optical coding and high quality security features to biochips", Nanotechnology, vol. 14, p. 1289-1311, 2003.

B. E. Baker, N. J. Kline, P. J. Treado, and M. J. Natan, "Solution-based assembly of metal surfaces by combinatorial methods", J. Am. Chem. Soc. V. 118, p. 8721-8722, 1996.

H.-G. Binger et al., "Interference enhanced surface Raman scattering of adsorbates on a silver-spacer-islands multilayer system", Molecular Physics, vol. 85, p. 587-606, 1995.

G. R. Brewer, Electron-Beam Technology in Microelectronic Fabrication, Academic Press, NY, 1980.

Michael M. Carrabba et al., "Substrate and Apparatus for Surface Enhanced Raman Spectroscopy" United States Patent, U.S. Pat. No. 5,255,067, Oct. 19, 1993.

S. Chan et al., "Surface Enhanced Raman Scattering of Small Molecules from Silver-coated silicon nanopore", Advanced Materials, 15, 1595-1598, 2003.

H. Fan et al. "Self-Assembly of Ordered, Robust, Three-Dimensional Gold Nanocrystal/Silica Arrays", Science, 304, 567-571, 2004.

S. Farquharson, et. al. "Material for Surface-Enhanced Raman Spectroscopy, and SER Sensors and Methods for Preparing Same", United States Patent, U.S. Pat. No. 6,623, 977, Sep. 23, 2003.

D. Ginger et al., "The evolution of Dip-Pen Nanolithography", Angew. Chem. Int. Ed. ,v. 43, p. 30-45, 2004.

N. Hales, et al. "Nanoparticle-based all-optical sensors", United States Patent, U.S. Pat. No. 6,778,316, Aug. 17, 2004.

K. Haupt, "Imprinted polymers-Tailor-made mimics of antibodies and receptors", Chem. Comm., 2003, 171-178.

S. Hayashi, "Spectroscopy of Gap Modes in Metal Particle-Surface Systems," Topics Applied Phys 81:71-95, 2001.

S. Hayashi et al., "A New method of surface plasmon excitation mediated by metallic nanoparticles", Jpn. J. Appl. Phys. Vol. 35, p. L331-L334, 1996.

W. R. Holland et al., "Surface-plasmon dispersion relation: shifts induced by the interaction with localized plasma resonances", Physical Review B, vol. 27, p. 7765-7768, 1983.

J. C. Hulteen et al., "Nanosphere lithography: Size-tunable silver nanoparticles and surface cluster arrays", J. Phys. Chem. B, v. 103, p. 3854-3863, 1999.

C. Keating et al., "Heightened Electromagnetic fields between Metal Nanoparticles: Surface Enhanced Raman Scattering from Metal-Cytochrome C-Metal Sandwiches", J. Phys. Chem B, 102, 9414-9425, 1998.

I-K. Kneipp et al. "Ultrasensitive Chemical Analyses by Raman Spectroscopy", Chem. Rev., 1999, vol. 99, p. 2957-2975, see p. 2971.

T. Kune et al., "Interaction between localized and propagating surface plasmons: Ag fine particles on Al surface" Solid State Communications, vol. 93, p. 171-175, 1995.

Lee P. C., Meisel, D. J., J. Phys. Chem., 86, p. 3391, 1982.

A. Leitner et al., "Optical properties of a metal island film close to a smooth metal surface", Applied Optics, vol 32, p. 102 -110, 1993.

Y. Lu et al., "Nanophotonic Crescent Moon Structures with Sharp Edge for Ultrasensitive Biomolecular Detections by Local Electromagnetic Field Enhancement Effect," Nano Letters, 5, 119-124, 2005.

V. Matyushin, A at al.,"Tuning the setup of sputter-coated multilayers in nanocluster-based signal enhancing biochips for optimal performance in protein and DNA-assays". Nanoscience and Nanotechnology Volume 4, pp. 98-105, 2004.

M. Moskovits, "Surface enhanced spectroscopy", Rev. Mod Phys., 57, 783, 1985.

T. Schalkhammer et al., "Reinforced cluster optical sensors", U.S. Pat. No. 6,669,906, Dec. 30, 2003.

G. C. Schatz, and R. P. Van Duyne, "Electromagnetic mechanism of Surface-enhanced spectroscopy", in Handbook of Vibrational Spectroscopy , J. M. Chalmers and P. R. Griffiths eds. (John Wiley & Son Ltd. 2002), p. 1-16.

H. S. Shin, et. al. "Direct patterning of silver colloids by microcontact printing: possibility as SERS substrate array", Vibrational Spectroscopy, v. 29, p. 79-82, 2002.

T. Takemori at al., "Optical response of a sphere coupled to a metal substrate", Journal of the Physical Society of Japan, vol. 56, p. 1587-1602, 1987.

Z. Wang et al., "The structural basis for Giant Enhancement Enabling Single-Molecule Raman Scattering", Proc. Nat. Acad. Sci. USA, vol. 100, p. 8638-8643, 2003.

J. West et al., "Metal Nanoshells for Biosensing Applications", U.S. Pat. No. 6,699724, Mar. 2, 2004.

D. Wiersma, "Localization of light in a disordered medium", Nature, 390, 671-673, 1997.

A. Wokaun, "Surface-enhanced electromagnetic processes", Solid State Physics, vol. 38, p. 223-295, 1984.

Y. Xia et al., "Template-assisted Self-Assembly of Spherical Colloids into Complex and Controllable Structures", Advanced Functional Materials, v. 13, p. 907-918, 2003.

J. Zheng et al., "Surface-enhanced Raman scattering of 4-Aminothiophenol in assemblies of nanosized particles and the macroscopic surface of Silver", Langmuir, vol. 19, p. 632-636, 2003.

S. Zou et al., "Silver nanoparticle array structures that produce giant enhancement in electromagnetic fields", Chem. Phys. Lett., 404, 62-67, 2005.

BACKGROUND OF THE INVENTION

A variety of methods for confinement of light and for localization and enhancement of electromagnetic field in nanostructures, for the purpose of enhancing various localized linear and nonlinear optical phenomena are known in the prior art (See, for example, A. Wokaun, 1984: M. Moskovits, 1985). Most attention in the prior art has been related to the phenomena of Surface Enhanced Raman Scattering (SERS), based on localization and confinement of light near the surfaces of substrates with nanoscale structure. SERS has proven to be a powerful analytical tool for ultra sensitive chemical and biochemical analysis (K. Kneipp et al., 1999).

One SERS-based structure that has been proposed employs an optical structure composed of a metal island film (MIF) over a smooth metal surface (H.-G. Binger et al., 1995, G. Bauer et al., 2003). A metal island film consists of a random two-dimensional array of metal particles, each of several (typically, 2-10) nm in largest size dimension. The shapes of the metal particles are also variable, so it is difficult to characterization the particles structurally. (The particles form a stochastic array of particles resembling oblate spheroids with all minor axis oriented normal to substrate surface, e.g., glass, quartz, or silicon.) For a variety of reasons that will become clear below.

The metal island film MIF is separated from a smooth metal layer by an intermediate spacer layer made from optically transparent dielectrical material, the thickness of which controls the strength of the interaction between the plasmons localized on the islands and the surface plasmons of smooth metal layer. The metal particles (islands) can be thought of as nanoscopic antennas, collecting the incident radiation and then transferring the energy into the nearby gap modes, that may be trapped into guided modes propagating in all directions in plane of surface (omnidirectional coupling). The ability of structure to absorb light at specific wavelength depends on the existence of an optimal spacer layer thickness that will maximize absorption in structure for specific wavelength close to that of excitation light (Leitner et al., Appl Opt 1993; W. R. Holland et al., 1983, T. Kune et al., 1995). For a variety of reasons that will become clear below, the maximum enhancement achievable with such MIF structures is limited to between about $10^6$-$10^8$.

The phenomenon of interaction of localized plasmons (LP) with surface plasmon polaritons (SPP) in plasmon materials has been discovered and new method of excitation of SPP in plasmon resonant smooth films mediated by nanoparticles has been proposed (S. Hayashi et al., 1996). An interesting phenomenon associated with SPP excitation is the generation of a strong electromagnetic field near the metallic surface. It is a generally accepted mechanism that a strong electromagnetic field leads to enhancement of various linear and nonlinear optical processes near the surface via a mechanism of surface-enhanced spectroscopy (M. Moskovits, 1985; G. C. Schatz and R. P. Van Duyne, 2002). According to this mechanism, the enhancement of SERS signal is proportional to $E^4$, where E is electromagnetic field near metal surface.

One typical application of this phenomenon is the surface enhanced Raman scattering of molecules adsorbed on metallic surfaces that support plasmon resonances at both the excitation and scattering wavelengths. Typical enhancement achieved by using electrolysis roughened silver or by using substrate prepared by nanosphere lithography (J. C. Hulteen et al., 1999) is in the range $10^6$-$10^8$. In general, the degree of enhancement seen is not uniform across the sensor nor reproducible.

The inability to control parameters of MIF metal surface and intrinsic limitations in size of metal particles to less than 5 nm (V. Matyushin, A et al., 2004) precludes their use for SERS (H.-G. Binger et al., 1995) limits the sensitivity of such a system since MIF-metal substrate structures do not have strong enhancement of Raman signal. Therefore MIF-metal substrate have been reduced to practice only for enhancement of fluorescence in so called "resonant nanocluster biochip" technology (G. Bauer et al., 2003; T. Schalkhammer et al., 2003).

SUMMARY OF THE INVENTION

The invention includes, in one aspect, an optical sensor for use with a visible or near infrared (NIR) laser excitation beam and a Raman spectroscopy detector, for detecting the presence of chemical groups in an analyte applied to the sensor. The sensor includes a substrate, a plasmon resonance mirror formed on a sensor surface of the substrate, a plasmon resonance particle layer disposed over the mirror, and an optically transparent dielectric layer about 2-40 nm thick separating the mirror and particle layer. The particle layer is composed of a periodic array of plasmon resonance particles having (i) a coating effective to binding analyte molecules, (ii) substantially uniform particle sizes and shapes in a selected size range between 50-200 nm (ii) a regular periodic particle-to-particle spacing less than the wavelength of the laser excitation beam. The particles may have high symmetry or reduced symmetry shape, and more generally, as will be considered below, may be spherical, spheroid, rod like, cylindrical, nanowire, tubes, toroid, or other shapes that, when uniform, can be arranged with regular periodicity. A particle layer, as defined herein, is also intended to encompass a regular array of holes in a planar plasmon layer, where the holes have the dimensions set out above for the particles. The device is capable of detecting analyte with an amplification factor of up to $10^{12}$-$10^{14}$, allowing detection of single analyte molecules.

The mirror may be a silver, gold or aluminum layer having a layer thickness between about 30-500 nm. The particle have a preferred dimension in a selected size range of between 50-150 nm, and may be formed from silver, gold, or aluminum solid or particles having a shell formed of such metals. In an exemplary embodiment, the mirror and particles are either both gold or both silver, and the particles are substantially spherical.

The particle layer may be formed of a regular array of closed packed plasmon resonance particles having a particle-to-particle spacing of about 20 nm of less, including direct particle-to-particle contact. The particle layer may include a periodic array of at least 50 particles in at least one direction, preferably at least 50 particles in each of two planar directions, e.g., orthogonal directions or directions diagonal directions dictated by close packing. The sensor may include one or more additional particle layers, each separated from the immediately underlying particle layer by an optical dielectric layer having a thickness of between 2-40 nm. The substrate may have a planar or curved shape, e.g., when formed on spherical beads or inside pores in a porous filter.

In another aspect, the invention includes a method of detecting chemical groups in an analyte with an amplification factor of at least $10^{10}$. In practicing the method, molecules of analyte are bound to plasmon resonant particles in the particle layer of an optical sensor of the type described above, the sensor surface is irradiated with a visible or NIR laser beam, and the Raman spectrum produced by the irradiating is recorded. The method may be effective to produce an amplification factor of at least $10^{12}$, and therefore capable of detecting chemical groups in one or a small number of analyte molecules. The method allows Raman spectrum analysis at an irradiating beam power as low as 1-100 μW (micro W).

These and other objects and features of the invention will be more fully understood when the following detailed description of the invention is read in conjunction with the accompanying drawings.

BRIEF DESCRIPTION OF THE DRAWINGS

FIGS. 2A and 2B show schematically the structure of GMs and SPPs in the same embodiment and illustrates in general how key principal mechanism of invention works.

FIGS. 3A and 3B shows an embodiment of the invention in which the periodic structure is a 2-dimensional array of nano-size holes in metallic film.

FIGS. 4A and 4B shows an embodiment of the invention in which the periodic structure is a 2-dimensional array of nano-size tubes imbedded in metallic film.

FIGS. 5A through 5D show an embodiment of the invention in which the periodic structure is a metallic grating consisting of a one-dimensional array of metallic strips or cylinders.

FIG. 15 Illustrates the use of a bead aerosol to detect distantly biological and chemical warfare agents and explosives with a Raman standoff system such as LIDAR;

DETAILED DESCRIPTION OF THE INVENTION

A. Definitions

Figure 1:
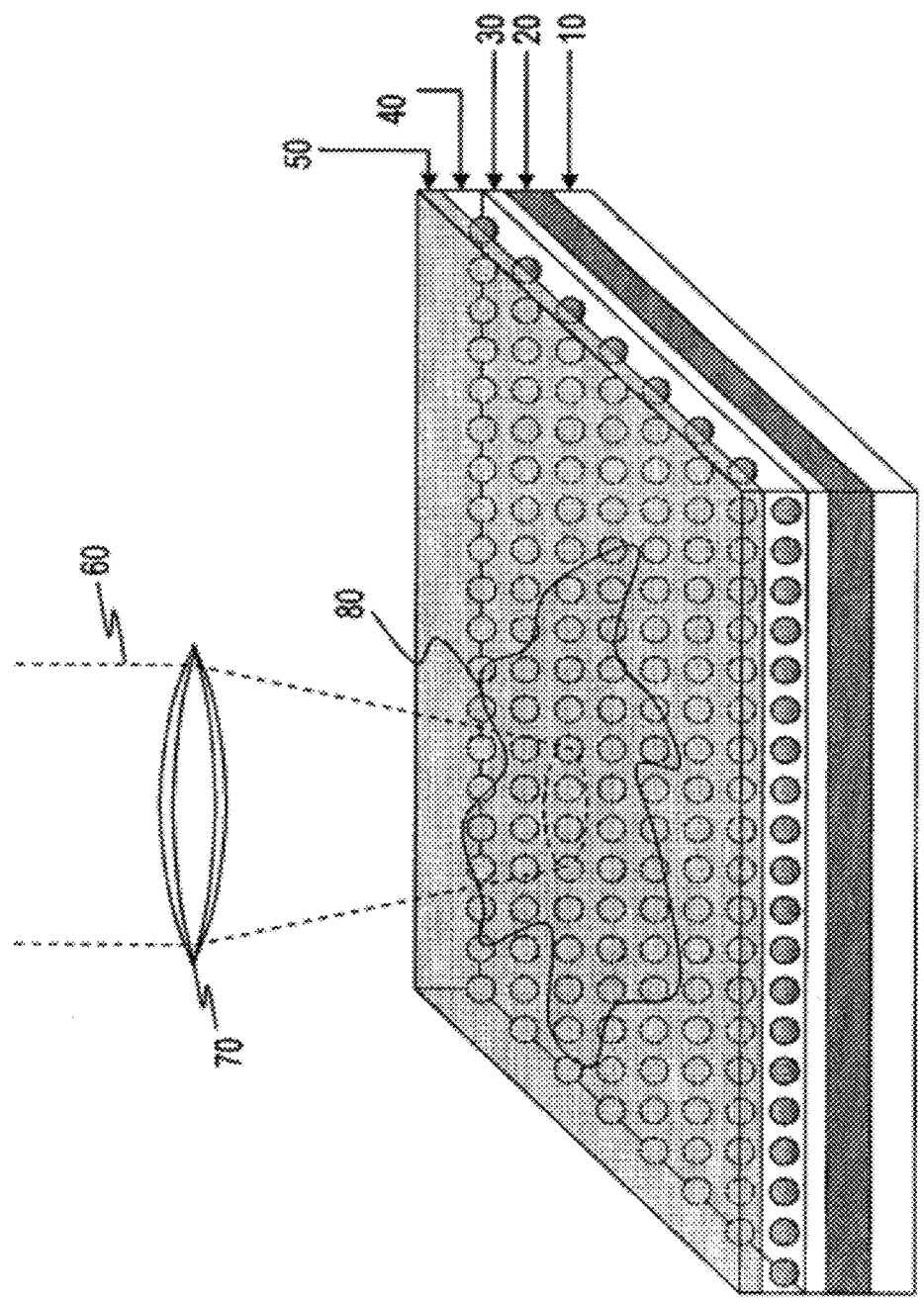
FIG. 1 shows the arrangement of components of a basic planar structure for confinement, localization, and enhancement of EM field according to one embodiment of the invention, and illustrates how it is used for measurement of SERS spectra.

The terms below have the following meaning, unless otherwise indicated.

"Plasmon resonant metal" includes any metal, such as gold, silver, or aluminum which can support surface electromagnetic modes—surface plasmon polaritons (SPP), which are coupled modes of photons and plasmons.

"Chemical group" in a sample may include subunits in a polymer, or subunit moieties, such as nucleic acid bases, or chemical constituent groups, such as hydroxyl, amine, alkyl, acid, or aldehyde groups. Such chemical groups are characterized by a unique enhanced Raman spectral signatures or features.

"Gap modes" or "GMs" refer to electromagnetic normal modes or electromagnetic eigenmodes that are excited by external electromagnetic field in a space between two or more plasmon resonance particles and when plasmon resonance particles are placed near (less than 40 nm) a metal surface, preferably a plasmon resonant metal surface.

"Plasmon resonance particles" (PRPs) are particles are particles formed of a plasmon-resonance metal, such as gold, silver, or aluminum, or particles having a shell of such metal. In the present invention, PRP have their largest dimension typically in the 50 nm to 200 nm size range.

"Gap-mode enhanced Raman spectrum" of a sample refers to spectral features in a Raman spectrum of the sample that are enhanced by the presence of gap modes at the sample.

"Photonic crystals" refers to 1-, 2-, 3-dimensional structures with periodic distribution of refraction index that results in a band-gap structure, with the result that photons with energies corresponding to this band gap cannot propagate on photonic crystal and may exist only in localized state.

"Photonic band gap" refers to a range of energy of photons in which they cannot propagate in photonic crystal structures.

"Visible light" refers to the portion of the electromagnetic spectrum that is visible to the human eye, generally in the wavelength range between 400 nm to 700 nm range.

"Near infrared" refers to the portion of the electromagnetic spectrum with a wavelength longer than visible light, but shorter than microwave radiation, generally in the wavelength range between 700 nm and 1 mm.

B. General Description of the Invention

The present invention provides a plasmon resonance nanostructure that allows precise control and tunability of its optical response through plasmon resonance effects. This is achieved by one or more periodic plasmon layers operating as 2-D or 3-D photonic crystals with appropriate photon band gap structure enhanced by coupling to a plasmon mirror through an optically transparent dielectric layer having a selected thickness of less than about 40 nm.

The general design of structure according to concept of the invention, which will be referred to "periodic plasmon nanostructure over plasmon mirror" consists of a continuous plasmon resonant material referred to as a "plasmon mirror" and at least one particle layer consisting of a 1-D or 2-D periodic array of plasmon resonance particles (or other regular nanostructures, as discussed below) in which localized plasmons (LPs) may be excited. Plasmon resonance coupling between the particle layer and mirror is through a selected-thickness, optically transparent dielectric layer having a selected "tuned" thickness between about 2-40 nm, preferably 2-20 nm.

The particles forming the particle layer are substantially uniform in size and shape, in a selected size range between about 50-200 nm, preferably 80-150 nm, depending on the excitation wavelength. The particles may have high symmetry or reduced symmetry shape, and more generally, as will be considered below, may be spherical, spheroid, rod like, cylindrical, nanowire, tubes, toroid, or other shapes that, when uniform, can be arranged with regular periodicity. They may be homogeneous consisting from one material—silver, or gold, or from composite such as nanoshells (J. West et al., "Metal Nanoshells for Biosensing Applications", U.S. Pat. No. 6,699724, Mar 2, 2004.). The periodicity of the particle layer(s), i.e., the spacing between adjacent particles in any direction, may vary from a close-packed arrangement, in which the particles are separated from one another by a spacing of between particle size plus 0-20 nm, or with a periodic spacing up to the wavelength of incident light, with optimal coupling and enhancement of signal being observed in the close-packed arrangement, preferably with spherical particles. A particle layer, as defined herein, is also intended to encompass a regular array of holes in a planar plasmon layer, where the holes have the dimensions set out above for the particles. The particles in the particle layer are separated by or embedded in a dielectric material which may be air or a solid, optically transparent dielectric material, such as like that forming the dielectric layer.

The plasmon resonance response of the nanostructure is tunable and may be controlled by adjustment of the parameters of the nanostructure including the spacing between layers, the size and shape of the nanoparticles, the spacing between nanoparticles, the periodicity of the particles forming the particle layer, and, and the dielectric constant and thickness of the dielectric layer. Maximum localization and enhancement of EM field is achieved when the frequency of the excitation light is the same as or close to the frequency of plasmon resonance of the nanostructure as a whole, or more precisely, the plasmon resonance frequency should be between the frequency of incident light and that of scattered light. Plasmon resonance frequency and shape of plasmon resonance response in such complex metal-dielectric nanostructure depends on many parameters (size, material, shape of nanoparticles, and their arrangement with respect to each other and with respect to plasmon mirror surface). However, strongest plasmon responses are obtained on dipole plasmon resonance excitations of LPs on isolated nanoparticles. Maximum confinement and localization and enhancement of the EM field in the structure is achieved through a mechanism of excitation of gap electromagnetic modes (GMs) or eigenmodes of the particle layer, and surface plasmon polariton modes (SPPs) excited on the smooth surface of the mirror. This mechanism operates through coupling and interactions between these modes and between the electromagnetic field of the excitation light.

An additional advantage of regular array of LP oscillators over a continuum of SPP under condition of coupling between them through GMs (close proximity between two layers separated by dielectric) is the mechanism of synchronization of LPs through SPPs that result in the narrowing of plasmon resonance and additional dramatic enhancement of local field and corresponding Raman signal. However, this effect exists in relatively narrow range of spectra. Typically the narrow collective plasmon resonances are in a range of 450-800 nm, but best enhancement achieved in range 500-600nm for silver NP and 600-750 nm for gold NP.

A general advantage of periodic regular array in the particle layer is that it now has both high plasmon resonant response and properties of a photonic crystal that result in additional effect of focusing and confinement of incident light beam due to confinement in photon band gap structure. This is in contrast to a random array of LPs over SPP continuum, where both effects synchronization between LP and focusing of incident light beam (by mechanism of Anderson localization disclosed in D. Wiersma, "Localization of light in a disordered medium", Nature, 390, 671-673 (1997)) are present, but overall the effect of EM field enhancement is significantly less, since the density of "hot spots" is relatively small. According to the generally accepted paradigm of SERS (M. Moskovits, 1985: G. Schats et al., 2002), enhancement of Raman signal happens through local field enhancement due to plasmon excitation in so called "hot spots." The general structure of "hot spots" in different array structures is explained and illustrated on FIGS. 2-5 below. From a practical stand point, this enhanced interaction from a periodic particle layer and plasmon mirror allows for a highly reproducible high quality Raman spectra with extremely low excitation power (typically 10-100 microwatt, and less than 1 microwatt for some samples).

The plasmon resonance nanostructure of the invention may be used in a variety of applications in analytical instrumentation, analytical chemistry and spectroscopy. As an example it may be used as a substrate in mass spectrometry devices for improvement of Laser Desorption Ionization, such as MALDI-TOF, SELDI-TOF). Another major field of use is enhancement of a variety of localized linear and nonlinear optical phenomena such as Generation of Harmonics, Coherent Anti-Stokes Raman scattering (CARS) and in particular as SERS-active substrate.

In particle, the nanostructure of the invention may be used for enhancement of Raman signal in various optical devices and optical sensor devices. In particular, one important practical application of the invention is its use as a SERS-active sensor for real-time all optical ultrasensitive detection and identification of chemical groups in chemical and biological analytes in samples in solid, liquid and gaseous environment. Four major embodiments of optical devices and optical sensors using these fundamental interactions are discussed below in Section D1-D4, and include:

1. Optical devices and sensors with planar SERS-active surfaces according to present invention (SERS-based), implemented, for example, in microfluidic chip platform;

2. Filter based optical devices and sensors with nonplanar SERS-active surfaces (SERS based) from optically transparent porous and mesoporous membranes and materials with all or part of internal surfaces covered by the resonant structure of present invention. This sensor is especially useful for continuous monitoring of environmental contaminants in liquid and gaseous phase;

3. Fiber optic coupled optical devices and sensor with both planar and nonplanar SERS-active surfaces (SERS based) for distant sensing (detection and identification) of environmental contaminants and hazardous materials; and 4. Mirobead based optical devices and sensors with nonplanar (spherical or spheroid shape) SERS-active surfaces (SERS based)—possible use are in microfluidic flow as well as in aerosol samples.

C. Basic Optical Sensor of the Invention

The structural requirement in the optical sensor of the invention can be understood from the following basic description of the physical interactions responsible for the giant EM enhancement it provides. Under plasmon resonance conditions, corresponding to plasmon oscillation of individual NPs, the EM field excites LP oscillation on each particle. For silver NPs in the range of 50-150 nm, plasmon resonance frequency is in a range 460-520 nm. This geometry of excitation is also optimal for excitation of two types of Gap electromagnetic modes (GMs). The first type is the GM between adjacent NPs in the layer array, and the second type, between NPs and the plasmon mirror surface. For efficient excitation of GMs, the spacing between adjacent particles (the periodicity of the layer) should be regular and less than wavelength of the EM field in the dielectric media (typically is 250-700 nm, since dielectric constant of transparent matrix and spacer layer is in a range 1.5-2.5), but best results are for a close-packed arrangement having a periodicity close to the diameter of the NPs plus up to 20 nm.

If the NP array (particle layer) is in close proximity to the plasmon surface (a distance less than about 40 nm), then SPPs in the mirror are excited and propagate in all directions in the surface plane. Due to coupling with the LPs of nanoparticles, SPPs creates a new mechanism (in addition to EM wave) of long range interaction between LP oscillations. Long range interactions produce synchronization of phases of LP oscillations in the NP array and results in narrowing bandwidth of plasmon resonance, so called collective plasmon oscillation. Optimal parameters for such synchronization to occur are: NP sizes in range 50-200 nm preferably 80-150 nm, and a regular periodicity (particle-to-particle spacing), preferably in both directions in the particle layer, of less than the wavelength of the excitation light, and preferably a close packed arrangement having a periodicity of the NP size plus up to 20 nm. Best amplification is achieved for a perfect periodic array with a number of NPs along one dimension of more than 50. Any deviation from perfect periodicity and from uniformity in NP size will reduce the enhancement effect since it results in disruption of synchronization and broadening of plasmon resonance shape. This explains why random arrays and fractal structures from NP are less efficient than the periodic nanostructure over plasmon mirror disclosed in the invention.

As an example of an exemplary nanostructure constructed in accordance with the invention, reference will be made to the optical sensor shown in FIGS. 1 and 2. The structure consists from substrate 10 providing an upper sensing surface. The substrate may be any dielectric support, such as glass, ceramic, or silicon waver slide or waver. Formed on the sensing surface of the substrate is a plasmon resonance mirror 20 which is formed from a material, such as silver, gold, or aluminum, capable of supporting surface plasmon polaritons (SPPs). This layer can be created by standard vacuum deposition technique (e.g., V. Matyushin, A et al., 2004). The thickness of the layer could be in a range 20-500 nm or more as long as it can function as a mirror surface in the optical range of spectra.

Spacer layer 30 formed over the mirror is composed from optically transparent dielectric material, for example, LiF formed by vacuum deposition, or dried polymer films, as described below. The thickness of layer is in a range less than 50 nm, preferably less than 40 nm, and more preferably 3-20 nm, e.g., 5-25 nm. If a self-assembling method is used for making the layer of nanoparticles on the dielectric layer, the layer is preferably formed of a polyamine or the like capable of forming covalent chemical bonds to the particles (and with the mirror layer). The dielectric spacer layer can be produced with a controlled thickness by using, for example, a micro-machined piezo driving system. In this case, the optical plasmonic properties of the substrate can be dynamically controlled to allow optimizing absorption maxima.

A nanoparticle layer 40 may be formed, for example, by a method of self assembling (B. E. Baker et al., 1996), which allow plasmon particles of any size (e.g., 80-100 nm sizes), employing particles with high uniformity in shape and size. Composite (Gold-Silver or Silica-Silver Shell) nanoparticles may also be used, as may low symmetry nanoparticles such as 'nanobowls' (Y. Lu et al., 2004). By using template directed self assembling techniques (Y. Xia et al., 2003) perfectly ordered (cubic or hexagonal or other symmetry) arrays of particles can be created with controlled surface density and interparticle distances. Plasmon particles can be covered by a protective layer individually.

A protective coating layer 50 may be, for example, formed from SiO or other dielectric optically transparent material. In an embodiment in which the particles have individual protective coating, a protective layer is not necessary. The thickness of the protective layer is less than 5 nm, preferably less than 2 nm. The protective layer or the coating on the individual particles may be derivatized with analyte binding molecules, such as antibodies, ligands, DNA fragments, and the like, or analyte binding to the coating or protective surface may be by non-specific absorption. In some embodiments, individual particles may be coated by a molecular imprinted polymer (MIP) to bind specific target analyte (K. Haupt, "Imprinted polymers-Tailor-made mimics of antibodies and receptors", Chem. Comm., 2003, 171-178) or by monoclonal antibodies for specific analytes. In either case, the surface of the sensor is exposed to analyte under conditions in which analyte molecules bind to the coating surface, typically placing the analyte within 0-5 nm from a PRE in the particle surface. However in some cases when analyte molecules may penetrate and bind directly to particle surface enhancement may be even larger. The figures show analyte molecules 80 placed on surface of coating 50.

In its optical sensing mode, the sensor surface is irradiated with a visible or NIR laser beam 60 through a focusing lens 70. As shown in FIGS. 2A and 2B, the incident light, indicated at 110, excites Gap Modes 130 (GMs) localized presumably within the particle layer and between the particles and the plasmon mirror, and gap modes 140 between nanoparticles (NPs) 100 forming the particle layer. Although not shown, localized plasmons (LPs) are formed about each particle. Surface plasmon polaritons (SPPs) formed on the surface of the metal film are shown at 150. The sinusoidal wave representation of the SPPs is intended to indicate that the SPPs are propagating, and not stationary. As seen, the GMs produce extremely high local electric field in close proximity to the particle surfaces. An end enhanced EM field results in enhancement of a Raman cross section that scales as $E^4$ (M. Moskovits, 1985: G. C. Schatz, and R. P. Van Duyne, 2002). Enhanced Raman signal light, indicated at 120, is generated by analyte molecules is collected in backscattering arrangement and is send to dispersive element of Raman spectrometer detector (not shown), where spectra of substance are analyzed and information about chemical groups is identified.

FIGS. 3-5 demonstrate other embodiments of "plasmon lattice over plasmon mirror" structure operating according to same general principle of work as described above. For example, in FIGS. 3A and 3B, the 2-D periodic plasmon structure is a metallic film 20a with a periodic array of nanoholes 102 with diameters in the range 20-200 nm and spacing between holes in a range less than wavelength of incident light. Between the plate with nanoholes 20b and a plasmon mirror 20a, there is dielectric layer 30 with thickness in the range 2-40 nm. Incident electromagnetic wave 110 excites LPs on the surface of each nanohole and SPPs 150 on the surface of the metal film. Due to resonance effects of anomalous transmission of light through array of subwavelenth nanoholes (T. Ebessen et al., Nature, 391, 667, 1998) electromagnetic field penetrates into the volume between the plasmon mirror and array of nanoholes and excites GMs 132 and two types of SPPs (shown at 150) in the surface of the plasmon mirror and on both surfaces of metal films with the array of nanoholes 20b. The SPPs and GMs interact with each other through the dielectric layer 30 of less than 40 nm thickness. Due to close proximity this additional long range interaction between SPPs and LPs stimulate synchronization of phases of LP oscillations in array and as a result plasmon resonance gets narrowed and local field on surfaces of NP substantially enhanced.

The nanohole lattice structure shown in FIGS. 3A and 3B may be formed, for example, by using photolithographic etch techniques to form a silver or gold layer containing an array of holes, each hole having a selected diameter in the 50-200 nm range, a firm thickness in the range 20-200 nm, and a hole-to-hole spacing in the range of up to the excitation wavelength and preferably in the range of hole diameter up to 20 nm. This film, once formed, can then be transferred to a structure containing the substrate mirror layer and dielectric layer to form the optical sensor nanostructure of the invention.

Analyte molecules 82 on the lattice layer may be adsorbed on the surface inside or near nanohole 102 and became exposed to strongly enhanced local field of NPs. Due to the SERS effect described above, Raman scattered signal 130 is enhanced, and this signal is detected by an optical system and subjected to spectral analysis in Raman spectrometer device.

FIGS. 4A and 4B illustrate similar embodiments to that presented on FIGS. 3A and 3B, except that the geometric parameters of the plasmon array lattice consist of metallic film 20b with sub-wavelength size holes and nanotubes 104 attached to each hole. The lattice period in this case has same range as that discussed, namely less than wavelength of the excitation light. The geometric structure of GMs between the lattice layer and mirror (shown at 134) will be slightly different with this configuration; however, the fundamental mechanism of interaction through excitation of LPs, GMs and SPPs and the effect of synchronization in an array of nanostructures is basically the same.

The nanotube lattice structure shown in FIGS. 4A and 4B may be formed, for example, by using self-assembly techniques to form an assembled array of sliver or gold nanotubes which are then transferred to a structure containing the substrate mirror layer and dielectric layer, to form the optical sensor nanostructure of the invention. Alternatively, the nanotube layer that is transferred to the mirror structure can be formed by photolithographic techniques in which both the tubes and the tube interiors are produced by etching of photoactivated regions of the array. In this embodiment, each tube has a selected ID in the 50-200 nm range, a film thickness (tube length) in the range 20-200 nm, and a tube-to-tube spacing in the range of up to the excitation wavelength and preferably in the range of tube diameter up to 20 nm.

It is worth noting that due to the symmetry of the lattice in FIGS. 2-4, the excitation of SPPs is omnidirectional and therefore the efficiency of excitation does not depend on polarization of incident light under perpendicular incidence geometry.

An alternative embodiment of the "plasmon lattice over plasmon mirror" structure is presented on FIGS. 5A-5D, which illustrates a structure in which the plasmon lattice is a 1-D array of nanocylinders 106 in FIGS. 5A and 5B or nanostrips 106 in FIGS. 5C and 5D which form, in effect, a plasmon metal grating as a lattice. (Other structures common to those shown in FIGS. 2-5 are identified with the same numerals in all of these figures). The range of geometric parameters is the same as in previous examples. All geometrical dimensions of the structure, including the diameter of the cylinders or strips, and the periodicity of the surface structures are less than wavelength of light. Specifically, each cylinder or strip has a selected OD or width in the 50-200 nm range, and the spacing between cylinders or widths of the strips is such as to give a periodicity of up to the wavelength of the excitation light and preferably the range cylinder OD (or strip width) plus up to 20 nm.

The nanocylinder lattice structure shown in FIGS. 5A and 5B may be formed, for example, by using self-assembly techniques to form an assembled array of sliver or gold nanocylinders which are then transferred to a structure containing the substrate mirror layer and dielectric layer, to form the optical sensor nanostructure of the invention. Alternatively, the nanocylinder layer that is transferred to the mirror structure is formed by photolithographic techniques.

The mechanism of operation through cylinder-to-cylinder GMs, indicated at 146, and cylinder-to-mirror GMs, indicated at 134, and SPPs, indicated at 150, are substantially the same as above. However, due to the reduced symmetry in 1-D, the excitation efficiency now depends on the orientation of polarization vector in lateral plane. More efficient excitation of GMs is achieved if the direction of the electric field in EM wave is perpendicular to the direction of cylinders and strips in lateral plane.

The principles of operation of SERS-active structures in optical sensor devices for analyte detection are the same as described in case of FIG. 2, and can be easily understood by analogy.

D. Description of Specific Embodiments

Figure 12A:
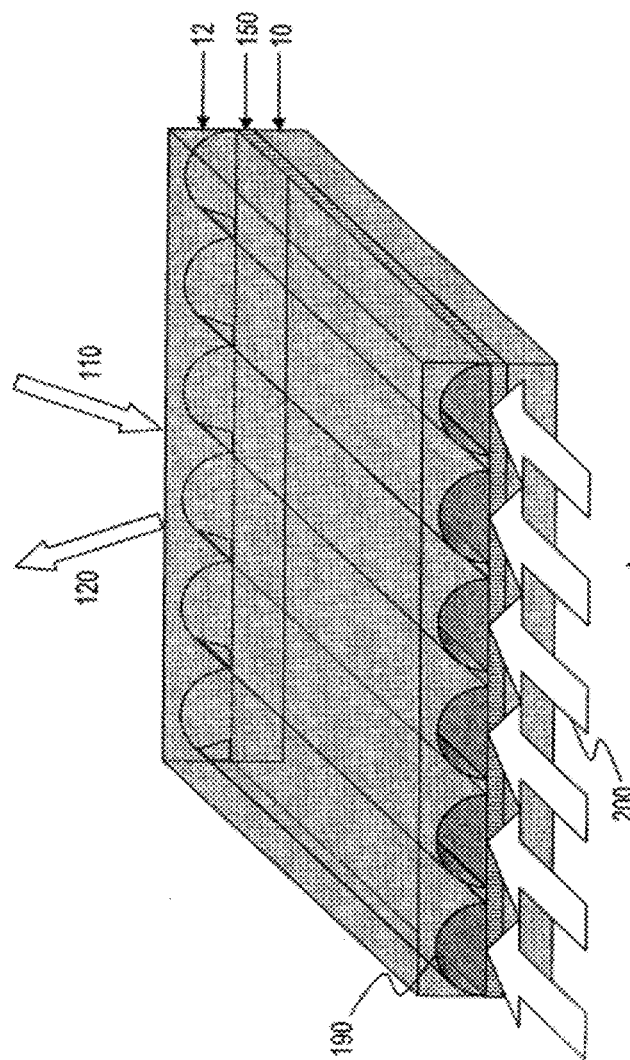
FIGS. 12A through 12D illustrate the use of SERS-active structure of the present invention integrated into a filter based optical SERS sensor with a planar (12A and B) and nonplanar (12C and D) SERS-active surface. The filter is made of an optically transparent porous silica. Part of the internal surface of the porous material is covered by the resonant SERS-active structure of the present invention.
Figure 12B:
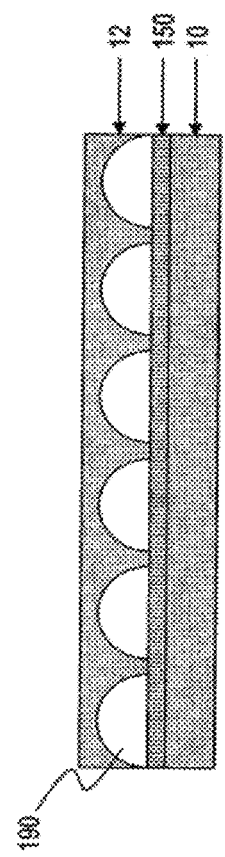
Figure 12D:
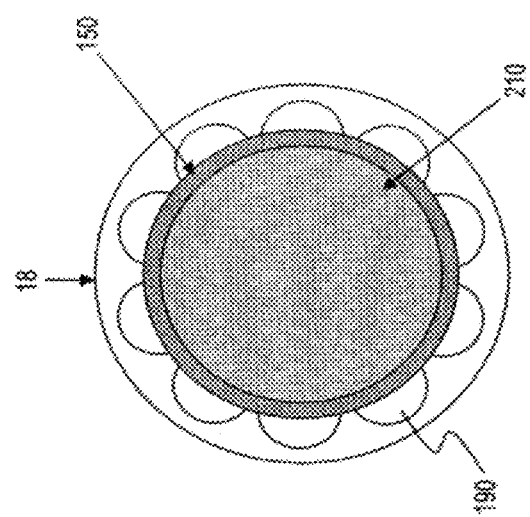
Figure 12C:
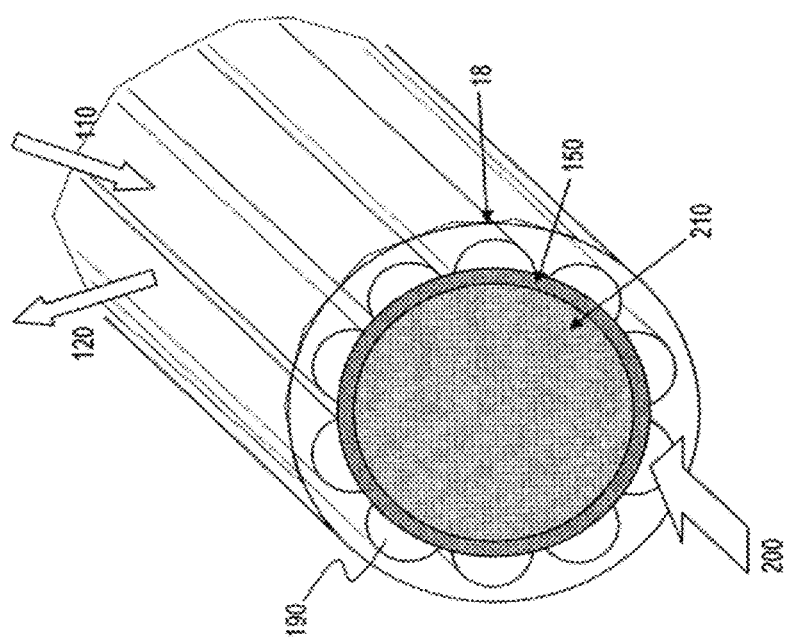

This section describes four applications of the optical nanostructures described above. In these embodiments, which are illustrated in FIGS. 12-16, the structure represented by numeral 150 in FIGS. 12 and 13 is the optical sensor nanostructure described above. For all embodiments, the range of optical nanostructures is intended to encompass the general structures described above.

D1. Planar Microfluidic Optical SERS Sensor

In its basic embodiment, the optical structures is used as an optical sensor for detection of analytes to which the sensor is exposed, e.g., in a planar microfluidic SERS chip platform that may be used for analysis of liquid samples with application to disease or environmental monitoring. The general schematic diagram of use of a planar microfluidic optical SERS sensor with a table top Raman microscope is illustrated on FIG. 16. The SERS active structure of present invention according to embodiments as illustrated in FIGS. 1-5 above may be integrated into each channel of a microfluidic chip 370 which is placed on a motorized translation table 360 and controlled by an electronic device 350 through a computer 180. Sample analyte flow through channels and analyte molecules are adsorbed into SERS-active surface and analyzed in Raman microscope. Light from a light source 300 through a beam splitter 312 and focusing optics 70 and microscope objective 72 is directed to a sample on the surface of SERS substrate. Raman signal generated in backscattering geometry through optical system is sent to dispersive element 330 and spectra are detected by CCD detector 340 and analyzed in computer 180. In another embodiment of sensor portable version of Raman spectrometer may be used. This sensor has broad range of use including, but not limited to: Environmental monitoring, Genomics and Proteomics research, DNA analysis, Pharmaceutical and Drug Industry, Agriculture and Food analysis, Biomedical diagnostics, Biodefence, Industrial monitoring, Forensic Analysis etc.

D2. Filter-based Optical SERS Sensor

That embodiment is illustrated the use of SERS-active structure of the present invention integrated into a filter based optical SERS sensor with a planar (12A and B) or nonplanar (12C and D) SERS-active surface. The SERS-active structure, indicated at 150, is integrated into porous filters made of optically transparent material such as porous silica in planar architecture as illustrated by FIGS. 12A and 12B. Filters from optically transparent porous silica may be the best for this sensor. Diameter of pores 190 may be in a range of 1-100 microns, depending on the purpose of the filter. The nanostructure 150 may be integrated into porous silica by coating pores by silver layer using electroless deposition method and subsequent functionalization of silver surface by nanoparticle as described in Example 1 and 2. A non-planar arrangement of pores covered with an SERS-active surface 150 is shown in FIG. 12C and D. With an analyte solution flowing through the filter, a laser system with spectrometer can be used for continuous monitoring of contaminants in solution or water 200 flowing through the pores of the filter 190. That is, the intended application is for continuous monitoring of contaminants and hazardous materials in a fluid system, such as a water supply system.

D3. Fiber Based Optical SERS Sensor

Figure 13A:
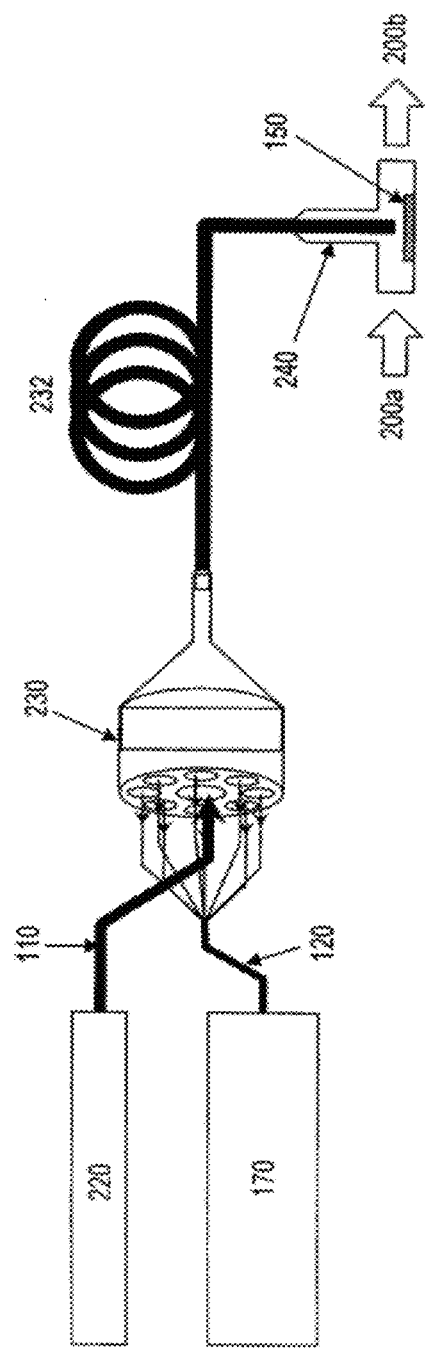
FIGS. 13A and 13B show a diagram of a fiber-optic coupled optical sensor for remote detection and identification of environmental contaminants and hazardous materials.
Figure 13B:
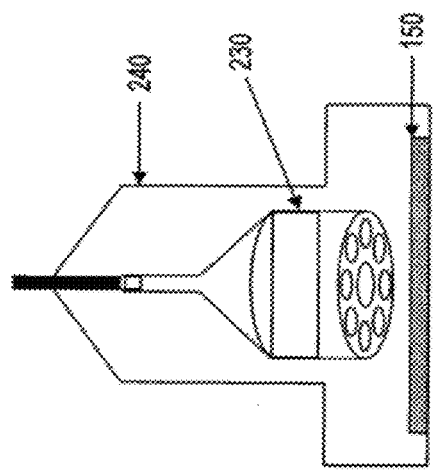

An application of the invention to a fiber optic sensor is illustrated by FIGS. 13A and B. Here the SERS-active structure 150 is integrated into a sensor probe 240 which is connected by an imaging fiber 232 (that contains between 1000 and 1000,000 of individual fibers fused together into single bundle) with a multichannel Raman analysis system 170. Excitation light from a light source 220 through fiber 232 is delivered to the SERS-active surface. Water with target analyte flows through a channel having an inflow 200a flow in and outflow 200b. Contaminants in the flow-through water are adsorbed to surface 150 and detected by enhanced Raman scattering. This type of sensor is particularly useful for applications involving monitoring the quality of an aqueous environment.

D4. Bead-based Optical SERS Sensor

Figure 14A:
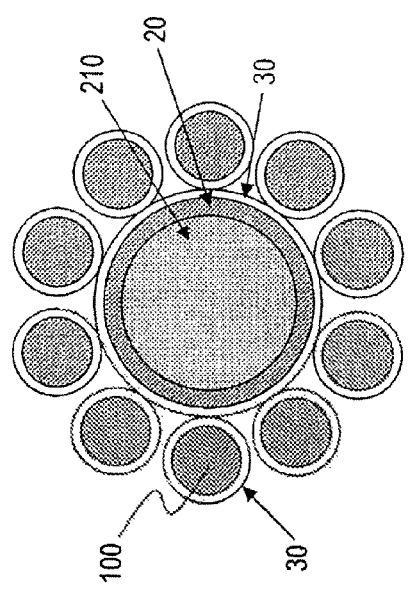
FIGS. 14A and 14B show a diagram of a microbead-based optical SERS sensor with a nonplanar spherical SERS-active surfaces.

In still another embodiment, the invention contemplates microbeads covered by the SERS-active coating of present invention, as illustrated in FIGS. 14A and B. Here, spherical beads 210 formed of polyester or a similar material and having diameters in the range 3-10 micron are covered by silver layer 20 by method of vacuum deposition, and this layer in turn is covered by a dielectric layer 30 having thickness in a range 2-40 nm. The coated bead is then covered by NPs 100 which have diameter in a range 50-150 nm. As shown, the NPs are also covered by dielectric coating 30. SERS-active beads can be used as a suspension in a microfluidic optical sensor device or in application requiring aerosols.

Figure 14B:
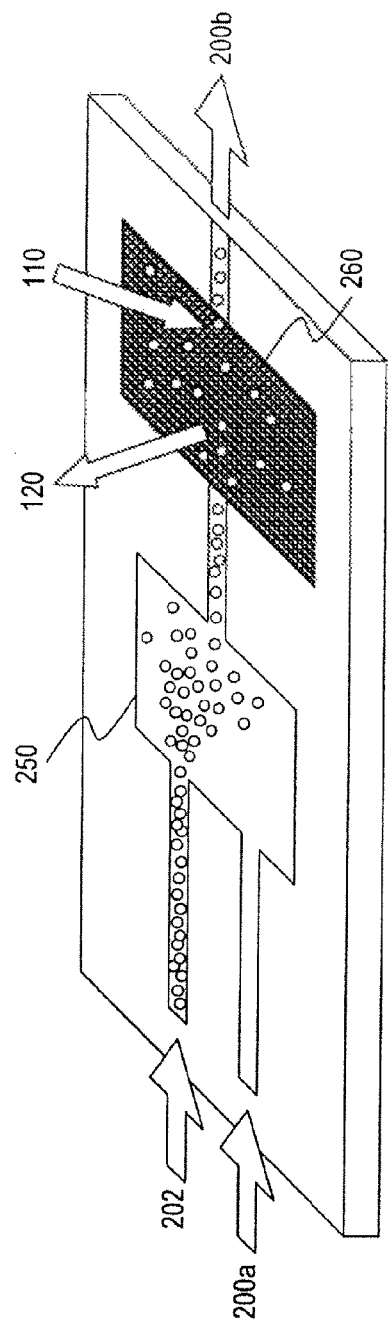
Figure 16:
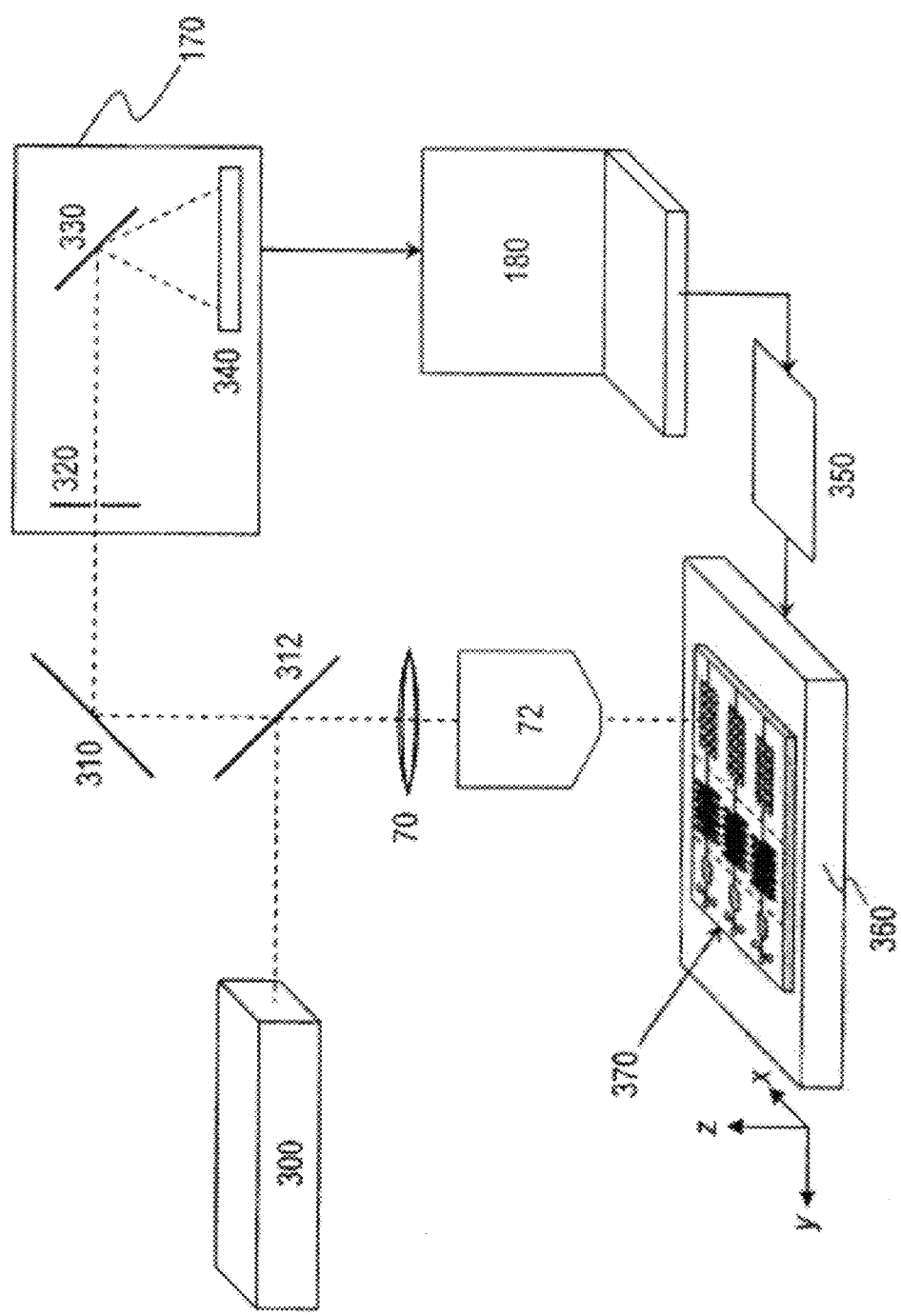
FIG. 16 Illustrates an embodiment of a planar microfluidic optical SERS sensor, in accordance with another embodiment of the invention.

The use of SERS-active beads in a microfluidic optical sensor is illustrated by FIG. 14B. Sample analyte in solution is injected through a channel 202 and suspension of SERS-active beads, through a channel 200. In mixing chamber 250 analyte is mixed with beads, and analyte molecules are adsorbed onto the surface of beads. In detection area 260 analyte is detected by SERS.

SERS-active beads in form of aerosol may be used for distant detection of warfare biological and chemical agents and explosives as illustrated by FIG. 15. here an aerosol of SERS-active beads 290 is injected from an injector 280 into a cloud 270 of gas to be analyzed. Analyte and beads are mixed in the cloud and analyte is adsorbed onto surface of SERS-active beads. Following this, the beads are collected, e.g., by a gas filter, or may be analyzed in situ by a Raman system 300 for example Raman LIDAR.

From the foregoing, it can be appreciated how various objects and features of the invention have been met. Model SERS plates constructed in accordance with the invention were prepared and tested with different Raman systems using adenosine molecule as analyte. A comparison of the results with that for a commercially available SERS plates and with an Intel porous silica covered by silver SERS plates demonstrates an amplification better at least 6 orders of magnitude over these prior art structures. The results are robust and reproducible, in that the same results were obtained on multiple different set nanostructures over a period of several months. The nanostructure plates are stable, since they sustain SERS activity for at least 3 month.

In accordance with the invention, and for the first time, substantial SERS signal in a range up to 7000 counts per second was obtained with new SERS plates at illumination power as low as 5 microW at sample and in some cases even 0.4 microWatt with R6G. This level of signal is comparable or better than that achieved in sensors based on luminescent detection; however required illumination power is at least 3 orders of magnitude less. Assuming an amplification factor of Intel substrates in a range $10^6$-$10^8$, one can estimate an amplification factor for SERS plates of present invention $10^{12}$-$10^{14}$.

The following examples illustrate various methods of forming and using the nanostructures of the invention, but are in no way intended to limit the scope of the invention.

EXAMPLE 1

Preparation of a Silver-silver Particle Nanostructure by Self-assembly of Ag Nanoparticles For each of a number of slides, a silver mirror was deposited on a clean glass microscope slide by thermal evaporation of the silver (99.995%) using vacuum deposition system (E302, Edwards). The slides were immersed in a 1% aqueous polylysine solution for one hour, forming a polylysine dielectric layer over the silver film. Following rinsing in copious amount of water, the slides were exposed overnight to a silver nanoparticle suspension of optical density 5 at extinction maximum of 450 nm. The self-assembly of the silver particles on the surface resulted in the yellow hue (appearance) of the mirrors. The slides were then rinsed with water and exposed to different analytes for various time periods. After the adsorption of analyte molecules slides were interrogated with Raman spectrometer yielding SERS spectra.

In the second example, silver nanoparticles were adsorbed on the surface of the mirror using poly(vinylpyridine) as the surface modifier (forming the dielectric layer). Poly(vinylpyridine) was adsorbed on the mirrored silver and gold surfaces from 1% ethanolic solutions for duration of several hours.

EXAMPLE 2

Preparation of Samples With Self Assembled Silver Particle Nanostructure by Microcontact Printing In this example, a method of microcontact printing as disclosed for example in reference (H. S. Shin, et. al. "Direct patterning of silver colloids by microcontact printing: possibility as SERS substrate array", Vibrational Spectroscopy, v. 29, p. 79-82, 2002, H. Fan et at., "Self-Assembly of Ordered, Robust, Three-Dimensional Gold Nanocrystal/Silica Arrays", Science, 304, 567-571 (2004), was used to form a close-packed array of silver nanoparticles on a silver mirror.

Silver nanoparticles were prepared by method disclosed in Lee P. C., Meisel, D. J., J. Phys. Chem., 86, p. 3391 (1982), Poly(vinyl pyrrolidone) was used as the capping agent. First, silver nitrate (0.2 g, Aldrich, 99+%) was dissolved into 3 mlL ethylene glycohol (Aldrich, 99.8%). 1 g polyvinyl pyrrolidone (Aldrich, MW ≈40 000) was added into 15 mL ethylene glycohol and the mixture was stirred and heated to 197° C. The silver nitrate in ethylene glycohol solution was subsequently injected into heated poly(vinyl pyrrolidone). This reaction mixture was then heated at 197° C. for 1 hour. The silver nanoparticles were precipitated by centrifugation. Specifically, the reaction mixture was cooled to room temperature, diluted with acetone (about 10 times by volume), and centrifuged at 4000 rpm for 20 min, with the liquid phase being removed using a pipette. The nanoparticles are rinsed with water, and washed with acetone and water for 2-3 times, to remove extra surfactants/polyvinyl pyrrolidone.

Glass slides used for silver deposition were first cleaned by soaking in NaOH (Aldrich, 99%) solution (0.1M NaOH in 75% ethanol aqueous solution). After 2 hours, glass slides are washed with ultrapure water and air-dried. A sliver thin film (thickness=100 nm) was deposited on the cleaned glass slides by Edwards EB3 e-beam evaporator in 432A. The obtained glass slides were soaked into 1 wt % poly(vinyl pyridine) (Sigma, Mw ≈37 500) solution. After 4 hours, the slides were rinsed with ultrapure water and air-dried. The slides were subsequently placed on a hot plate and baked at 50° C. for 15 minutes.

Silver nanoparticles in hexane solution were carefully dropped onto water surface, where the hexane spreads on the water surface to form a thin oil film. As hexane evaporates, the film surface shrinks until all the hexane is gone and silver nanoparticles are self-assembled into a close-packed monolayer.

These silver monolayers were transferred to the slice surface by bringing the slide parallel to the water surface and lightly touching the substrate to the nanoparticle film. Multiple layers of silver nanoparticle could be achieved by repeating this process. (shown as followed figure)

The slides were baked on a hot plate at 50° C. for 15 minutes.

The method used in slide preparation is similar to method disclosed in H. S. Shin, et. al. "Direct patterning of silver colloids by microcontact printing: possibility as SERS substrate array", Vibrational Spectroscopy, v. 29, p. 79-82, 2002, H. Fan et al., "Self-Assembly of Ordered, Robust, Three-Dimensional Gold Nanocrystal/Silica Arrays", Science, 304, 567-571, 2004.

Figure 6:
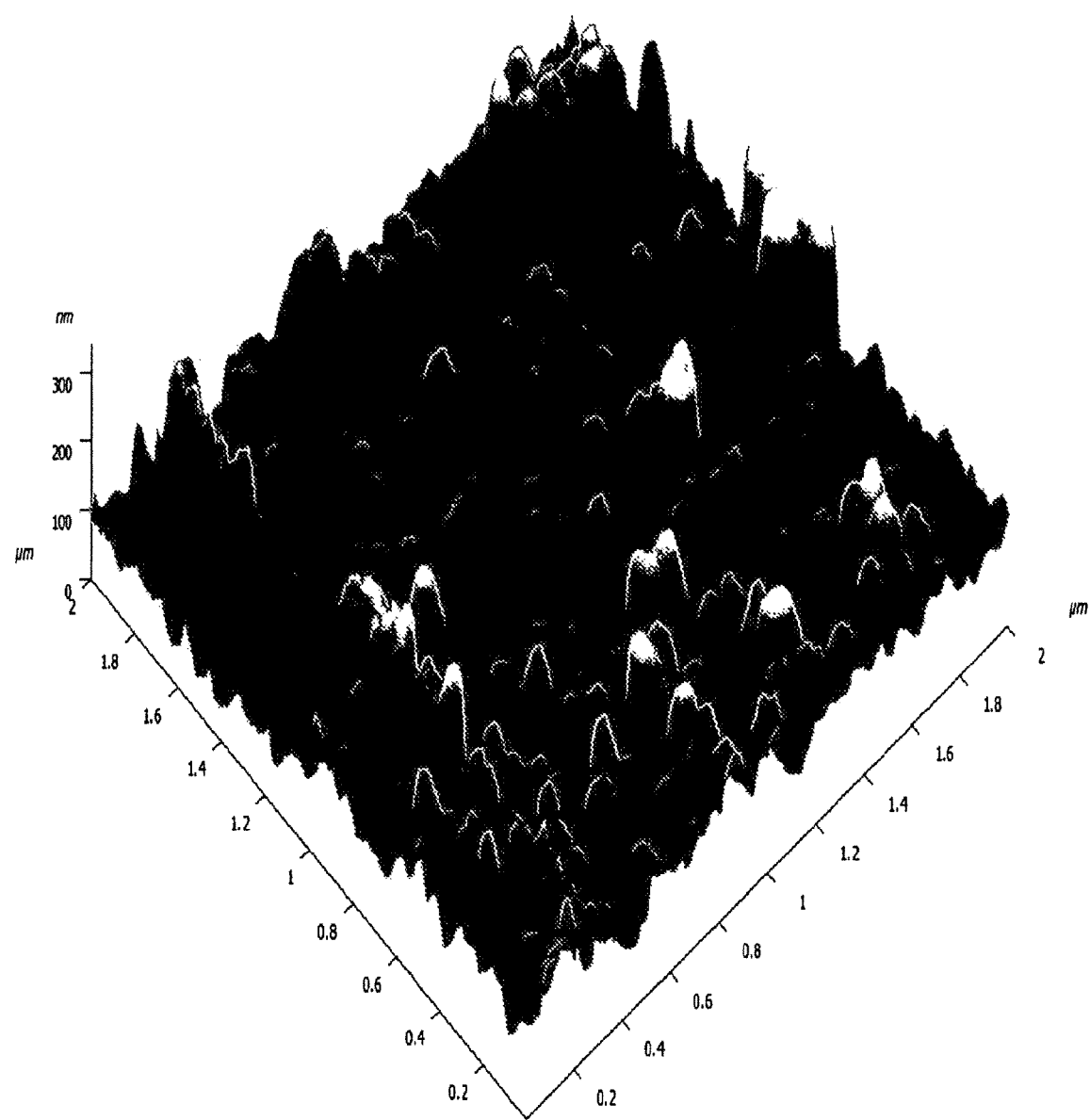
FIG. 6 is an AFM topographic image of a 2 micron by 2 micron area of surface of a planar SERS-active substrate fabricated according to Example 2. The image demonstrates the uniformity and high density of packing of nanoparticle placement on the surface.

An AFM topographic image of typical SERS substrate prepared by this protocol is presented in FIG. 6, showing a high density array of NP is close to periodic structure.

EXAMPLE 3

Experimental Measurements on the Analyte Rhodamine 6 G (R6G)

Figure 7A:
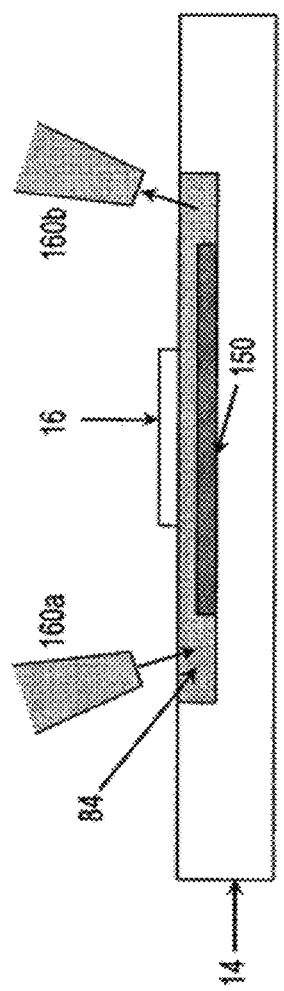
FIGS. 7A-7C show various aspects of an experimental set up with a Raman microscope and fluidic cell used for measurement of SERS spectra from liquid samples.
Figure 7B:
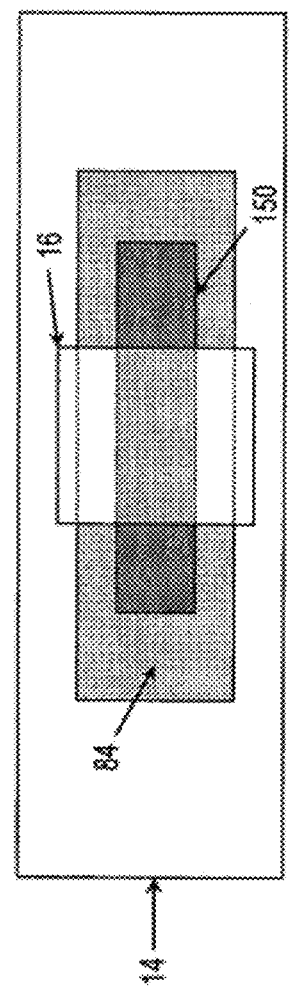
Figure 7C:
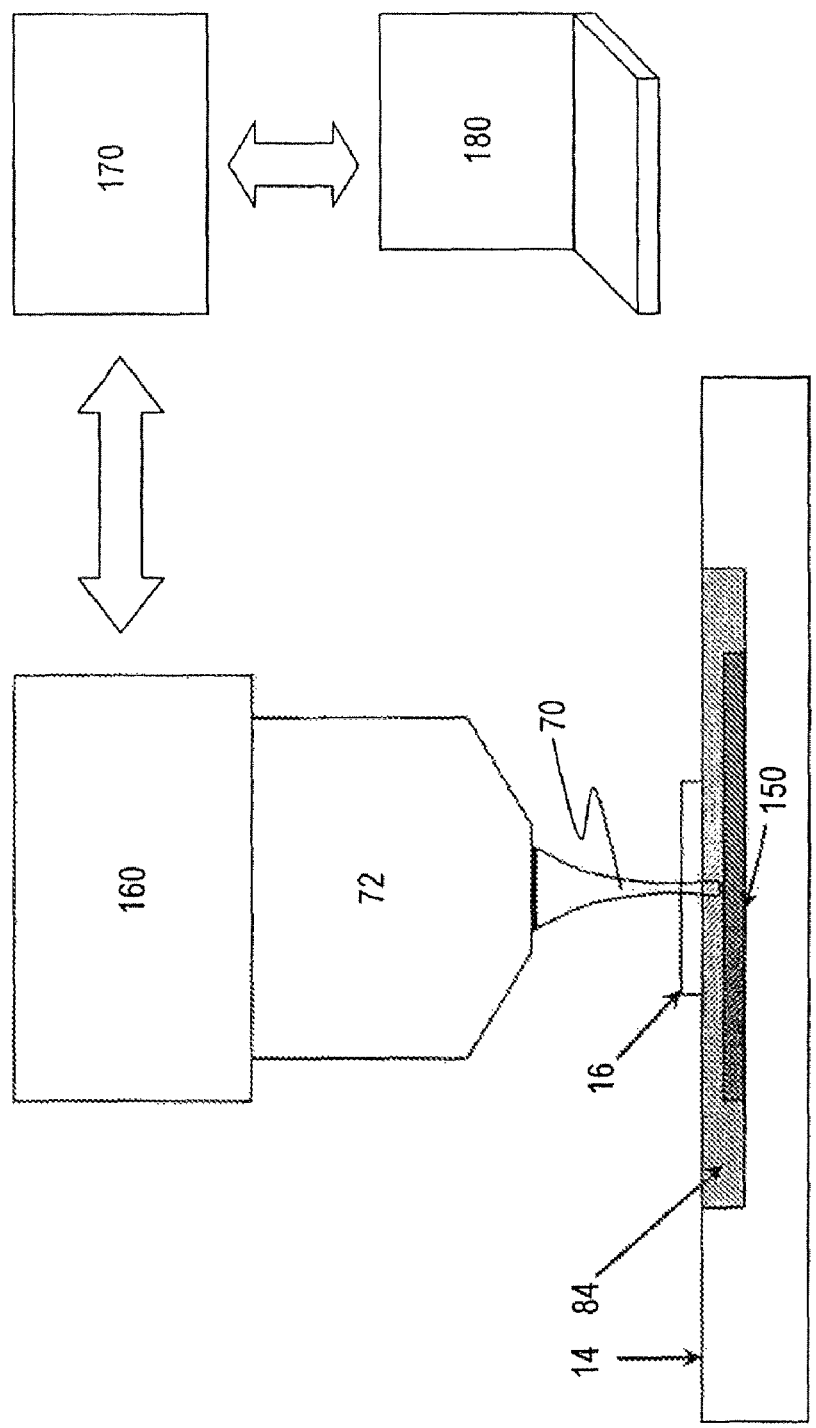

The experimental system set up used in present experiments is shown on FIG. 7A-7C. Measurements were carried using Horiba-Jobin Yvon Raman microscope LabRam HR 800.

Measurement of SERS spectra from liquid samples was carried out using a fluidic cell made from borosilicate glass. A schematic diagram of a fluidic cell is presented on FIG. 7A (top view) and in FIG. 7B (cross sectional view). A glass fluidic cell contains fluidic a channel 84 formed on a glass slide 14 to a depth of about 1.2 to 2.0 mm. The thickness' of the SERS-active structure 150 was 0.8 mm. During the experiment, the optimal value of parameters such as depth of fluidic channel was determined, e.g., the best conditions for focusing of the laser light beam through the confocal objective in Raman microscope. Use of the glass cover slip 16 was critical in order to maintain the same thickness of analyte layer during all sets of measurements. As a result an optimum depth of fluidic channel of about 1.5 mm was determined.

Use of the fluidic cell also allows for determining an accurate detection limit for analytes in solution, in terms of concentration of analyte molecules in solution measured in units of mole/liter. For that purposes a Langmuir adsorption isotherm was determined for each analyte.

Aqueous solutions of Rhodamine 6 G (R6G) were prepared in a range of concentrations from lowest $10^{-10}$ moles/l up to $10^{-3}$ moles/l. As a first step, measurements of Raman spectra were taken from solutions with the lowest concentration of analyte and subsequent measurement were done with the same SERS-active plate but with increasing concentration of analyte. At each step of the procedure, analyte solution was injected into the fluidic cell using a pipette 160a, then covered by glass cover slip. After measurement of the Raman spectra, analyte solution was replaced by a new one at higher concentration, and the measurement was repeated under conditions of focusing the illumination beam. The focus of the Raman microscope was adjusted to obtain optimal illumination condition, and these settings were used for all subsequent measurements. During each next step, solution in fluidic cell was replaced by solution with increasing concentration of analyte, using pipette 160b to remove analyte solution.

FIG. 7C shows the experimental setup employed in the measurements. In this figure, optical sensor nanostructure 150 is irradiated by an optical beam 70 which is focused by a lens assembly 72. Scattered light from the sample is focused in assembly 72, and directed by a beam-splitter 160 to a multichannel Raman analysis system 170, with spectral analysis carried out on computer 180. This method allows for the use of the same SERS-active substrate in multiple measurements. It also allowed for testing the robustness of the substrate.

The results of representative experimental data obtained with R6G using fluidic cell 1.5 mm deep and Raman microscope Horiba-Jobin Yvon LabRam HR 800 are shown on FIGS. 8 to 11. From these data, the quantitative limit of detection (LOD) was determined for R6G to be 100 nano M/l. The LOD was define as the first concentration at which distinctive spectral features of R6G first appeared in Raman spectra.

Figure 8:
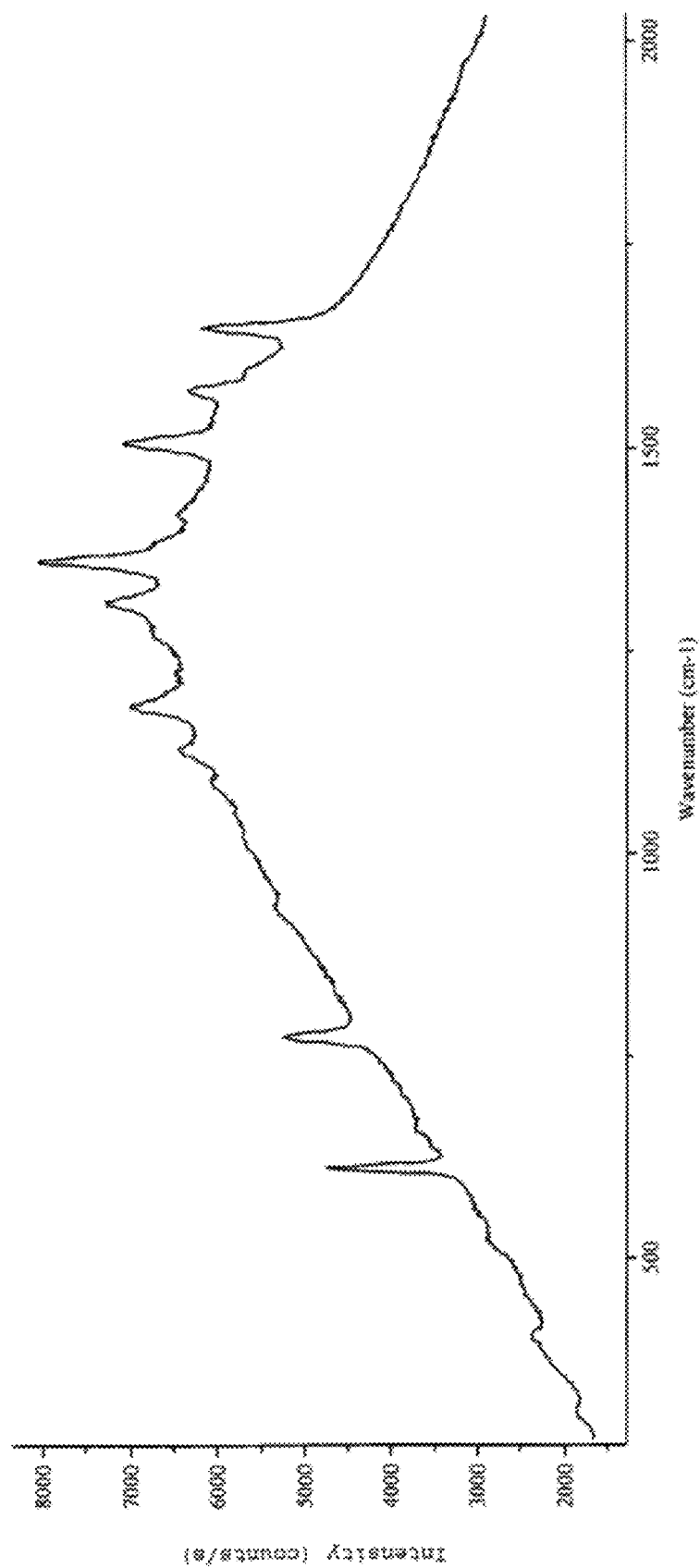
FIG. 8 shows a SERS spectra for Rhodamine 6G (R6G) molecules obtained in a fluidic cell using a Raman microscope Horiba-Jobin-Yvon Lab Ram HR 800 and Argon laser.

FIG. 8 show SERS spectra of R6G at concentration 500 nanoM/L, with a laser power at sample of 4.1 µW, integration time 10 sec, wavelength of excitation light beam 514 nm, objective 50×/0.45, with the light beam focused on the surface of the substrate, and a diameter of focal spot at sample of 2 micron. This spectra was obtained without subtraction of background. It can be seen that that even at very low illumination power, Raman signal is very strong, yielding 7000 counts per second for strongest lines.

Figure 9:
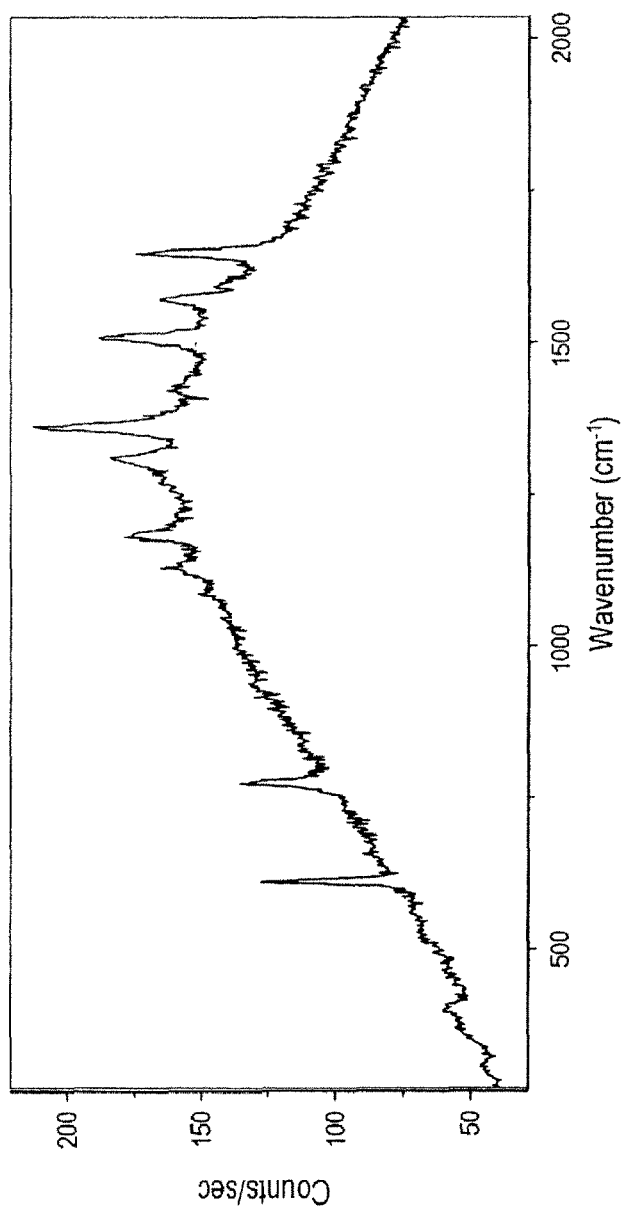
FIG. 9. shows a SERS spectra of Rhodamine 6G molecules obtained in fluidic cell using Raman microscope.

FIG. 9 shows SERS spectra of R6G at the same conditions and set up as for the FIG. 8 experiment, except that the excitation power at the sample was extremely small, as low as 0.4 µW. Although the Raman signal is less in this case (about 200 counts per second), the signal to noise ratio that characterizes a quality SERS spectra is still is very high, more than 100.

Figure 10A:
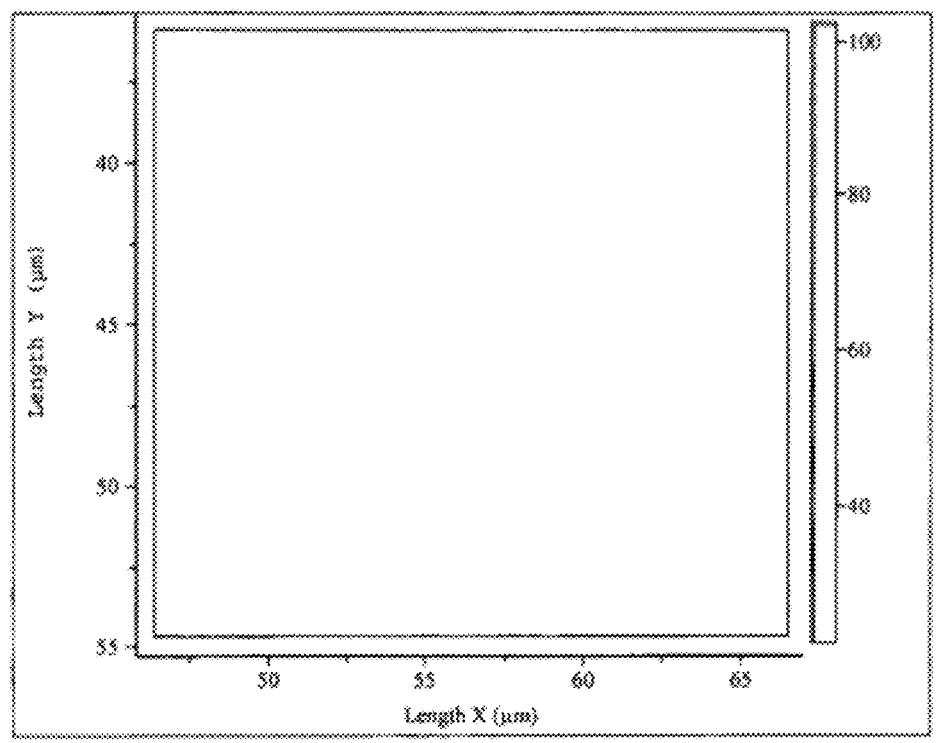
FIG. 10A is a Raman image of 20×20 μ area for main intensity peak (1280 and 1400 cm-1) of Rhodamine 6 G molecules with a baseline correction in %.
Figure 10B:
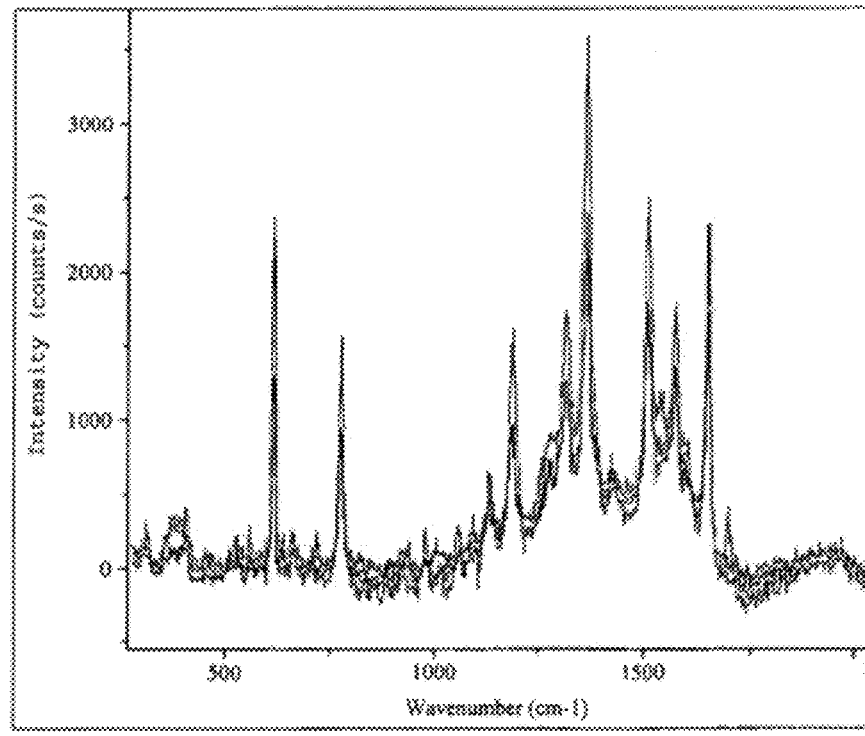
FIG. 10B is a SERS spectra of Rhodamine 6 G molecules at maximum and minimum intensity with baseline correction.

FIGS. 10A and 10B show Raman spectra images obtained by mapping a 20 micron by 20 micron area of SERS substrate. Excitation power in this experiment was 32 µW, collection time for each individual spectra was 1 second, mapped area was 20×20 micron, and the measurement of map was done with a 1 micron step and a total number of spectra was 400 points. The whole map was done for 7 min using automated motorized table system of Horiba-Jobin Yvon LabRam HR 800 Raman Microscope.

FIG. 10A shows a Raman image for intensity of main peak of R6G, integrated over the interval 1280-1400 cm$^{-1}$ with baseline correction, where intensity is given in %. The results show high uniformity across the surface of enhancement properties of SERS-substrate according to present invention. Maximum variation of intensity of major spectral feature is less than 25% as illustrated by FIG. 10B, where spectra with maximum and minimum intensity are presented for comparison.

Figure 11A:
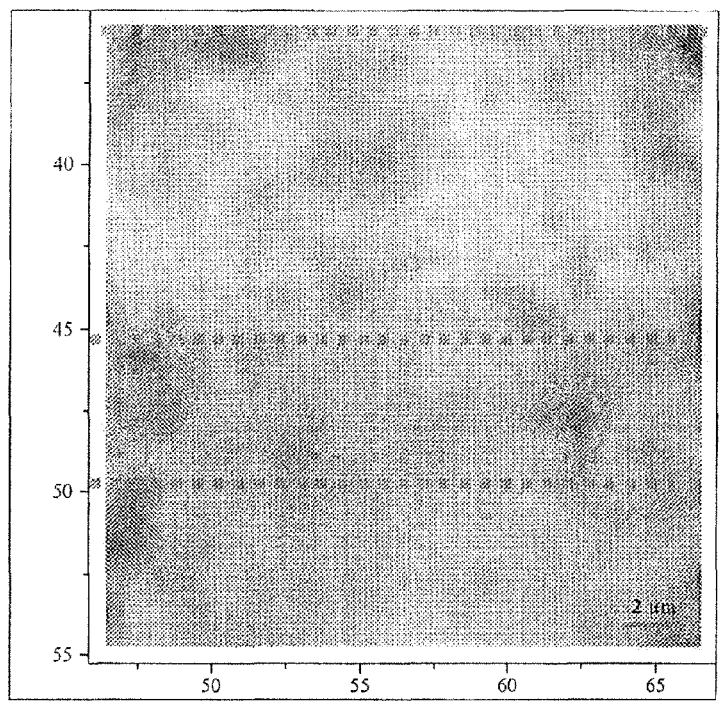
FIG. 11A is a Raman imaging map of Rhodamine 6G (R6G) molecules on SERS slide of area 20×20 micron. Dotted lines present spots from which Raman spectra have been collected.
Figure 11B:
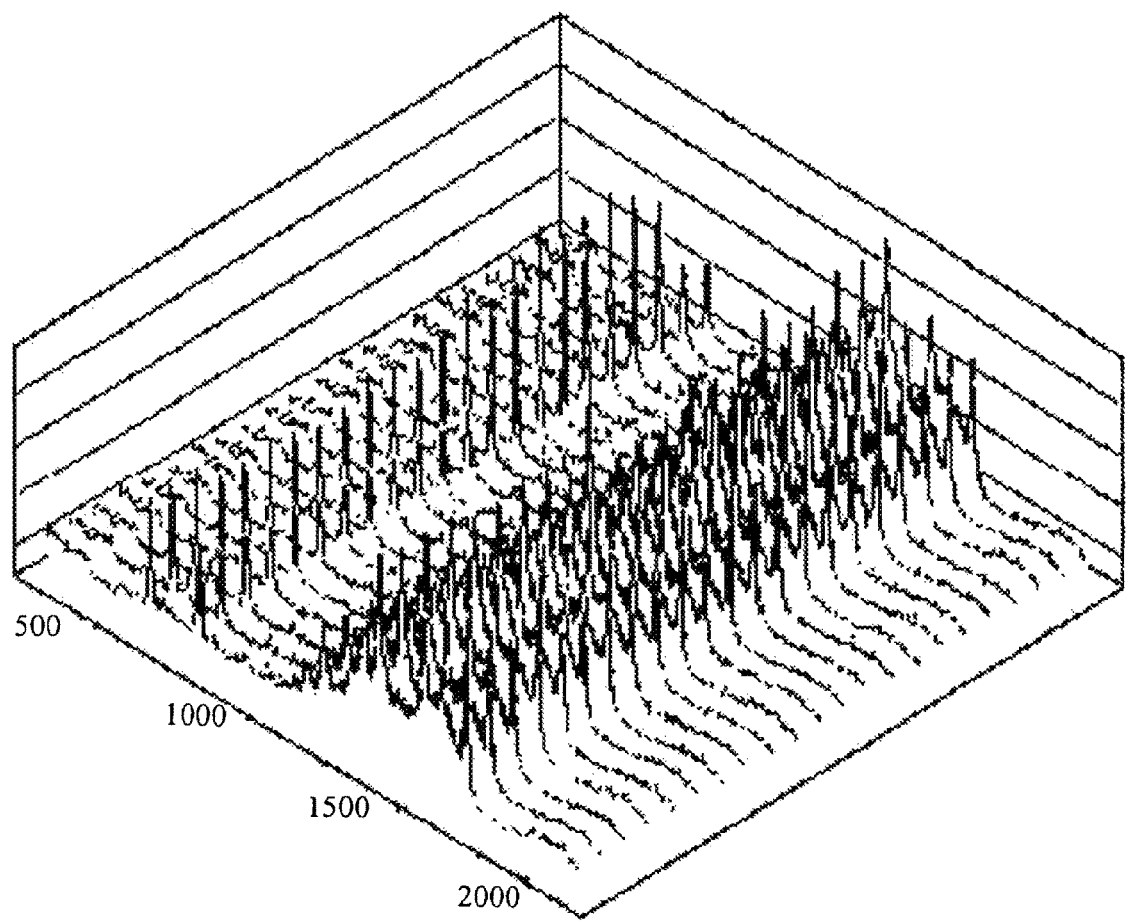
FIG. 11B is a SERS spectra of Rhodamine 6G molecule along Line 1 out of 21, from the top of map demonstrating uniformity of "hot spots" across the surface of substrate.

FIGS. 11A and 11B show the same data, but where the set of SERS spectra are along one line consisting of 20 points, presented as a 3-D plot in FIG. 11B.

The data demonstrate high uniformity across the surface of the enhancement properties of SERS-substrate in the present invention, meaning that a high density of "hot spot" that is critical for practical use of SERS-substrate is achieved, and shows the superiority of this SERS-substrate over others available in prior art.

in particular, it has been discovered that substrates prepared by the present invention have unusually strong enhancement of Raman signal compared with other SERS substrates. Most impressive is the fact that a strong Raman signal is achieved even at 0.4 microWatt of illumination power (See data presented on FIG. 9). Experimental data show that SERS plates of the present invention exceed the amplification of Raman signals achievable in the currently existing SERS plates developed by Intel Precision Biology Group (S. Chan et al., "Surface Enhanced Raman Scattering of Small Molecules from Silver-coated silicon nanopore", Advanced Materials, 15, 1595-1598, 2003, at least 5 to 6 orders of magnitude. This means that the substrate of present invention can provide a reproducible and stable amplification factor up to $10^{12}$ to $10^{14}$, where allowing for single molecule sensitivity.

While the invention has been described with respect to certain embodiments and applications, it will be appreciated how various modifications and changes, and additional applications can be made without departing from the invention.

It is claimed:

1. A microbead composition for use in detecting chemical groups in an analyte with an amplification factor of at least $10^{10}$ comprising
a collection of microbeads, each composed of (a) a microbead substrate; (b) a plasmon resonance mirror formed on the surface of the substrate, (c) disposed over said mirror, a dielectric layer having a thickness of 2-40 nm, and (d) a plasmon resonance particle layer composed of a periodic array of plasmon resonance particles in a selected size range between 50-200 nm and having a coating effective to bind analyte molecules,
wherein binding of analyte to the microbeads, and analysis of the microbeads and bound analyte by Surface Enhanced Raman Scattering is effective to produce a Raman spectrum of the chemical groups in the analyte with an amplification factor of at least $10^{10}$.

2. The microbead composition of claim 1, wherein microbead substrates have a diameter in the range 3-10 microns.

3. The microbead composition of claim 1, wherein the plasmon resonance particles are substantially uniformly distributed over the surface of the mirror coating on the microbead substrate.

4. The microbead composition of claim 3, wherein the plasmon resonance particles are also coated with a dielectric layer.

5. The microbead composition of claim 1, which is effective to produce a Raman spectrum of the chemical groups in the analyte with an amplification factor of at least $10^{12}$.

6. The microbead composition of claim 1, wherein the plasmon resonance mirror has a thickness of between about 30 nm to about 500 nm.

7. The microbead composition of claim 1, wherein the plasmon resonance mirror is made from a material selected from silver, gold, or aluminum.

* * * * *